(12) United States Patent
Selker et al.

(10) Patent No.: US 8,207,142 B2
(45) Date of Patent: Jun. 26, 2012

(54) INHIBITOR OF DNA METHYLATION

(75) Inventors: Eric U. Selker, Eugene, OR (US);
Cindy B. Matsen, Chicago, IL (US);
Peter A. Jones, La Canada, CA (US);
Jonathan Cheng, Alhambra, CA (US);
Sheldon B. Greer, Aventura, FL (US);
Victor E. Marquez, Montgomery Village, MD (US)

(73) Assignees: The United States of America as represented by the Secretary of the Department of Health and Human Services, Washington, DC (US);
University of Oregon, Eugene, OR (US); University of Miami School of Medicine, Miami, FL (US); University of Sounthern California, Los Angeles, CA (US); University of Miami, Miami, FL (US)

( * ) Notice: Subject to any disclaimer, the term of this patent is extended or adjusted under 35 U.S.C. 154(b) by 418 days.

(21) Appl. No.: 10/485,438

(22) PCT Filed: Jul. 30, 2002

(86) PCT No.: PCT/US02/24223
§ 371 (c)(1),
(2), (4) Date: Jan. 30, 2004

(87) PCT Pub. No.: WO03/012051
PCT Pub. Date: Feb. 13, 2003

(65) Prior Publication Data
US 2005/0119201 A1 Jun. 2, 2005

Related U.S. Application Data

(60) Provisional application No. 60/309,242, filed on Jul. 31, 2001, provisional application No. 60/311,435, filed on Aug. 10, 2001.

(51) Int. Cl.
*A61K 31/7068* (2006.01)
(52) U.S. Cl. .......................................... 514/49; 514/274
(58) Field of Classification Search .................... 514/49, 514/274
See application file for complete search history.

(56) References Cited

U.S. PATENT DOCUMENTS
4,894,364 A 1/1990 Greer
(Continued)

FOREIGN PATENT DOCUMENTS
JP 08-510385 11/1996
(Continued)

OTHER PUBLICATIONS

Droz, et al. (1998) Expert Opin. Investig. Drugs, 7(7): 1139-57 (Abstract Only).*

(Continued)

*Primary Examiner* — Timothy Thomas
(74) *Attorney, Agent, or Firm* — Klarquist Sparkman, LLP

(57) ABSTRACT

Zebularine has hypomethylating activity, and can be used to inhibit, reverse, and/or reduce DNA methylation in vivo and in vitro. Methods are provided for treating methylation-linked conditions through the application of 2-pyrimidinone derivatives, such as Zebularine. Compositions, including pharmaceutical compositions, comprising such derivatives are also provided. Also provided are kits for use in inhibiting DNA methylation, which kits include an amount of a 2-pyrimidinone derivative.

6 Claims, 15 Drawing Sheets

U.S. PATENT DOCUMENTS

| | | | |
|---|---|---|---|
| 5,470,974 | A | 11/1995 | Summerton et al. |
| 5,503,975 | A | 4/1996 | Smith et al. |
| 5,607,925 | A | 3/1997 | Matthews |
| 5,728,684 | A | 3/1998 | Cheng et al. |
| 5,786,146 | A | 7/1998 | Herman et al. |
| 5,871,917 | A | 2/1999 | Duffy |
| 5,872,104 | A | 2/1999 | Vermeulen et al. |
| 6,011,200 | A | 1/2000 | Dellaporta et al. |
| 6,017,704 | A | 1/2000 | Herman et al. |
| 6,020,139 | A | 2/2000 | Schwartz et al. |
| 6,184,211 | B1 | 2/2001 | Szyf |
| 6,200,756 | B1 | 3/2001 | Herman et al. |
| 6,214,556 | B1 | 4/2001 | Olek et al. |
| 6,251,594 | B1 | 6/2001 | Gonzalgo et al. |
| 6,255,293 | B1 | 7/2001 | Kimchi |

FOREIGN PATENT DOCUMENTS

| | | |
|---|---|---|
| WO | WO 94/27632 | 12/1994 |
| WO | WO 00/51639 | 9/2000 |
| WO | WO 00/70090 | 11/2000 |
| WO | WO2005/082144 | 9/2005 |

OTHER PUBLICATIONS

Driscoll, et al. (1991) J. Med. Chem., 34: 3280-84.*
Jeong, et al. (1998) J. Med. Chem., 41: 2572-78.*
Dammann, Richaed et al, Hypermethylation of the CpG Islaand of Ras Asso. Domain Family . . . , Can cer Research, Apr. 2002, vol. 61, pp. 3105-3109.*
Hurd et al:, Mechanism based Inhibition . . . , J.Mol.Biol., 1999. vol. 286, pp. 389-401.*
Egger et al., Epigenetics in Human Disease . . . , Epigenetics in human disease and prospects for epigenetic therapy, 2004, vol. 429, pp. 457-463.*
Patani et al.; "Bioisosterism: A Rational Approach in Drug Design"; 1996; Chem. Rev.; 96: 3147-3176.*
Moyer et al.; "Inhibition of Uridine Kinase and the Salvage of Uridine by Modified Pyrimidine Nucleosides"; 1985; Molecular Pharmacology; 28: 454-460.*
Murphy et al.; DNA Alkylating Agents Alleviate Silencing of Class II Transactivator Gene Expression in L1210 Lymphoma Cells; 2002; J. Immunol.; 169: 2085-3093.*
Avramis et al.; Pharmacology of combination chemotherapy of cytosine arabinoside (ara-C) and uracil arabinoside (ara-U) or tetrahydrouridine (THU) against murine leukemia L1210/0 in tumor-bearing mice; PubMed abstract; PMID: 3664332.*
Avvedimento et al., "Reactivation of Thyroglobulin Gene Expression in Transformed Thyroid Cells by 5-Azacytidine," *Cell* 58: 1135-1142, Sep. 22, 1989.
Bender et al., "Inhibition of DNA Methylation by 5-Aza-2'—deoxycytidine Suppresses the Growth of Human Tumor Cell Lines," *Cancer Research* 58: 95-101, Jan. 1, 1998.
Benedict et al., "Induction of Morphological Transformation in Mouse C3H/10T½ Clone 8 Cells and Chromosomal Damage in Hamster $A(T_1)Cl-3$ Cells by Cancer Chemotherapeutic Agents," *Cancer Research* 37: 2202-2208, Jul. 1977.
Broday et al., "5-Azacytidine Induces Transgene Silencing by DNA Methylation in Chinese Hamster Cells," *Molecular and Cellular Biology* 19(4): 3198-3204, Apr. 1999.
Bouck et al., "Induction of a Step in Carcinogenesis That Is Normally Associated with Mutagenesis by Nonmutagenic Concentrations of 5-Azacytidine," *Molecular and Cellular Biology* 4(7): 1231-1237, Jul. 1984.
Chiu and Blau, "5-Azacytidine Permits Gene Activation in a Previously Noninducible Cell Type," *Cell* 40: 417-424, Feb. 1985.
Christman et al., "Formation of Highly Stable Complexes between 5-Azacytosine-substituted DNA and Specific Non-histone Nuclear Proteins," *J. Biol. Chem.* 260(7): 4059-4068, Apr. 10, 1985.
Christman et al., "Correlation between Hypomethylation of DNA and Expression of Globin Genes in Friend Erythroleukemia Cells," *Eur. J. Biochem.* 81: 53-61, 1977.
Čihák, A., "Biological Effects of 5-Azacytidine in Eukaryotes," *Oncology* 30: 405-422, 1974.
Compere and Palmiter, "DNA Methylation Controls the Inducibility of the Mouse Metallothionein-I Gene in Lymphoid Cells," *Cell* 25: 233-240, Jul. 1981.
Constantinides et al., "Phenotypic Conversion of Cultured Mouse Embryo Cells by Aza Pyrimidine Nucleosides," *Developmental Biology* 66: 57-71, 1978.
Creusot et al., "Inhibition of DNA Methyltransferase and Induction of Friend Erythroleukemia Cell Differentiation by 5-Azacytidine and 5-Aza-2'—deoxycytidine," *J. Biol. Chem.*257(4): 2041-2048, Feb. 25, 1982.
Darmon et al., "5-Azacytidine is able to induce the conversion of teratocarcinoma-derived mesenchymal cells into epithelial cells," *The EMBO Journal* 3(5): 961-967, 1984.
Ginder et al., "Activation of a chicken embryonic globin gene in adult erythroid cells by 5-azacytidine and sodium butyrate," *Proc. Natl. Acad. Sci. USA* 81: 3954-3958, Jul. 1984.
Groudine et al., "Chromatin structure of endogenous retroviral genes and activation by an inhibitor of DNA methylation," *Nature* 292: 311-317, Jul. 23, 1981.
Hansen and Gartler, "5-Azacytidine-induced reactivation of the human X chromosome-linked *PGK1* gene is associated with a large region of cytosine demethylation in the 5' CpG island," *Proc. Natl. Acad. Sci. USA* 87: 4174-4178, Jun. 1990.
Hepburn et al., "The Role of Cytosine Methylation in the Control of Nopaline Synthase Gene Expression in a Plant Tumor," *Journal of Molecular and Applied Genetics* 2: 315-329, 1983.
Hossain et al., "5-Azacytidine (5Az) induces apoptosis in PC12 cells: a model for 5Az-induced apoptosis in developing neuronal cells," *Histol. Histopathol.* 12: 439-445, 1997.
Hossain et al., "5-Azacytidine induces toxicity in PC12 cells by apoptosis," *Exp. Toxic Pathol.* 49: 201-206, 1997.
Hsiao et al., "Effects of 5-Azacytidine on the Progressive Nature of Cell Transformation," *Molecular and Cellular Biology* 5(7): 1800-1803, Jul. 1985.
Jaenisch et al., "Treatment of mice with 5-azacytidine efficiently activates silent retroviral genomes in different tissues," *Proc. Natl. Acad. Sci. USA* 82: 1451-1455, Mar. 1985.
John and Amasino, "Extensive Changes in DNA Methylation Patterns Accompany Activation of a Silent T-DNA *ipt* Gene in *Agrobacterium tumefaciens*—Transformed Plant Cells," *Molecular and Cellular Biology* 9(10): 4298-4303, Oct. 1989.
Jones, P., "Altering Gene Expression with 5-Azacytidine," *Cell* 40: 485-486, Mar. 1985.
Jones and Taylor, "Cellular Differentiation, Cytidine Analogs and DNA Methylation," *Cell* 20: 85-93, May 1980.
Karpf et al., "Inhibition of DNA methyltransferase stimulates the expression of signal transducer and activator of transcription 1, 2, and 3 genes in colon tumor cells," *PNAS* 96(24): 14007-14012, Nov. 23, 1999.
Ley et al., "DNA methylation and regulation of the human β-globin-like genes in mouse erythroleukemia cells containing human chromosome 11," *Proc. Natl. Acad. Sci. USA* 81: 6618-6622, Nov. 1984.
Michalowsky and Jones, "Differential Nuclear Protein Binding to 5-Azacytosine-Containing DNA as a Potential Mechanism for 5-Aza-2'—Deoxycytidine Resistance," *Molecular and Cellular Biology* 7: 3076-3083, Sep. 1987.
Neves et al., "rRNA gene activity and control of expression mediated by methylation and imprinting during embryo development in wheat × rye hybrids," *Theor. appl. Genet.* 91: 529-533, 1995.
Niwa and Sugahara, "5-Azacytidine induction of mouse endogenous type C virus and suppression of DNA methylation," *Proc. Natl. Acad. Sci. USA* 78(10): 6290-6294, Oct. 1981.
Persengiev and Kilpatrick, "The DNA methyltransferase inhibitor 5-azacytidine specifically alters the expression of helix-loop-helix proteins Id1, Id2 and Id3 during neuronal differentiation," *NeuroReport* 8: 2091-2095, Jul. 1997.
Prakash and Kumar, "Inhibition of shoot induction by 5-azacytidine and 5-aza-2'—deoxycytidine in *Petunia* involves DNA hypomethylation," *Plant Cell Reports* 16: 719-724, 1997.
Reitz, Jr. et al., "DNA Methylation and Expression of HLA-DRα," *Molecular and Cellular Biology* 4(5): 890-897, May 1984.

Santi et al., "Covalent bond formation between a DNA-cytosine methyltransferase and DNA containing 5-azacytosine," *Proc. Natl. Acad. Sci. USA* 81: 6993-6997, Nov. 1984.

Taylor and Jones, "Multiple New Phenotypes Induced in 10T½ and 3T3 Cells Treated with 5-Azacytidine," *Cell* 17: 771-779, Aug. 1979.

Viegas-Pequignot and Dutrillaux, "Segmentation of human chromosomes induced by 5-ACR (5-azacytidine)," *Hum. Genet.* 34: 247-254, 1976.

Vieira et al., "1R chromosome nucleolus organizer region activation by 5-azacytidine in wheat × rye hybrids," *Genome* 33: 707-712, 1990.

Constantinides et al., "Functional striated muscle cells form non-myoblast precursors following 5-azacytidine treatment," *Nature* 267: 364-366, May 1977.

Barchi et al. "The Decomposition of 1-(β-D-Ribofuranosyl)-1,2-dihydropyrimidin-2-one (Zebularine) in Alkali: Mechanism and Products," *J. Org. Chem.*, 57:536-541, 1992.

Barchi et al., "Improved Synthesis of Zebularine [1-(β-D-Ribofuranosyl)-dihydropyrimidin-2-one] Nucleotides as Inhibitors of Human Deoxycytidylate Deaminase," *J. Enzyme Inhibition*, 9:147-162, 1995.

Barchi et al., "Inhibition of Cytidine Deaminase by Derivatives of 1-(β-D-Ribofuranosyl)-dihydropyrimidin-2-one (Zebularine)," *Nucleosides & Nucleotides*, 11:1781-1793, 1992.

Barletta et al., "Methylation of HSV-1 DNA as a mechanism of viral inhibition: studies of an analogue of methyldeoxycytidine: trifluoromethyldeoxycytidine ($F_3$mdCyd)," *Antiviral Res.*,18:1-25, 1992.

Bender et al., "Inhibition of DNA methylation by 5-aza-2'-deoxycytidine suppresses the growth of human tumor cell lines," *Cancer Res.*, 58(1):95-101, Jan. 1, 1995, Abstract Only.

Boothman et al., "Exploitation of Elevated Pyrimidine Deaminating Enzymes for Selective Chemotherapy," *Pharmac* 42:65-99, 1989.

Boothman et al., "Metabolic Channeling of 5-Fluoro-2'-deoxycytidine Utilizing Inhibitors of Its Deamination in Cell Culture," *Mol. Pharmacology*, 27:584-594, 1985.

Boothman et al., "Tumor-selective Metabolism of 5-Fluoro-2'-deoxycytidine Coadministered with Tetrahydrouridine compared to 5-Fluorouracil in Mice Bearing Lewis Lung Carcinoma[1]," *Cancer Res.*, 47:2354-2362, May 1, 1987.

Cambareri et al., "Epigenetic Control of a Transposon-Inactivated Gene in *Neurospora* is Dependent on DNA Methylation," *Genetics*, 143:137-146, May 1996. p. 137 only.

Cambareri et al., "Repeat-Induced C-G to A-T Mutations in *Neurospora*." *Science*, 244:1571-1575, Jun. 30, 1989.

Carlow and Wolfenden, "Substrate Connectivity Effects in the Transition State of Cytidine Deaminase," *Biochemistry*, 37:11873-11878, 1998.

Driscoll et al., "Antitumor Properties pf 2(1*H*)-Pyrimidinone Riboside (Zebularine) and Its Fluorinated Analogues," *J. Med. Chem.*, 34:3280-3284, 1991.

Eads et al., "Epigenetic patterns in the progression of esophageal adenocarcinoma," *Cancer Res.*, 61(8):3410-3418, Apr. 15, 2001, Abstract Only.

Eads et al., "MethyLight: a high-throughput assay to measure DNA methylation," *Nucleic Acids. Res.*, 28(8):i-viii, 2000.

Feil et al., "Developmental control of allelic methylation in the imprinted mouse *Igf2* and *H19* genes," *Development*, 120:2933-2943, 1994.

Foss et al., "Abnormal Chromosome Behavior in *Neurospora* Mutants Defective in DNA Methylation," *Science*, 262:1737-1741, Dec. 10, 1993.

Foss et al., "Mutations in the *dim-1* gene of *Neurospora crassa* reduce the level of DNA methylation," *Mol. Gen. Genet.* 259:60-71, 1998.

Frick et al., "Binding of Pyrimidin-2-one Ribonucleoside by Cytidine Deaminase as the Transition-State Analogue 3,4-Dihydrouridine and the Contribution of the 4-Hydroxyl Group to Its Binding Affinity," *Biochemistry*, 28: 9423-9430, 1989.

Frommer et al., "A genomic sequencing protocol that yields a positive display of 5-methylcytosine residues in individual DNA strands," *Proc. Natl. Acad Sci. USA*, 89:1827-1831, Mar. 1992.

Ferguson et al., "High frequency of hypermethylation at the 14-3-3 σ locus leads to gene silencing in breast cancer," *PNAS*, 97(11):6049-6054, May 23, 2000.

Gonzalez-Zulueta et al., "Methylation of the 5' CpG island of the p16/CDKN2 tumor suppressor gene in normal and transformed human tissues correlates with gene silencing," *Cancer Res.*, 55(20):4531-4535, Oct. 15, 1995, Abstract only.

Gonzalgo et al., "Rapid quantitation of methylation differences at specific sites using methylation-sensitive single nucleotide primer extension (Ms-SNuPE)" *Nuc. Acids Res.* 25(12):2529-2531, 1997.

Hagemann et al., "Control and Function of DNA Methylation in *Neurospora crassa*" *Epigenetic Mech. of Gene Reg.*, pp. 335-344, 1996.

Hurd et al., "Mechanism-based Inhibition of C5-cytosine DNA Methyltransferases by 2-H Pyrimidinone," *J. Mol. Biol.*, 286:389-401, 1999.

Jeong et al., "Carbocyclic Analogues of the Potent Cytidine Deaminase Inhibitor 1-(β-D-Ribofuranosyl)-1,2-dihydropyrimidin-2-one (Zebularine)," *J. Med. Chem.*, 41:2572-2578, 1998.

Jones, "Death and methylation," *Nature*, 409:141-143, Jan. 11, 2001.

Jütterman et al., "Toxicity of 5-aza-2'-deoxycytidine to mammalian cells is mediated primarily by covalent trapping of DNA methyltransferase that than DNA demethylation," *Proc. Natl. Sci. USA*, 91:11797-11801, Dec. 1994.

Kim et al., "Synthesis of Pyrimidin-2-one Nucleosides as Acid-Stable Inhibitors of Cytidine Deaminase," *J. Med. Chem.*, 29:1374-1380, 1986.

Laliberté et al., "Potent inhibitors for the deamination of cytosine arabinoside and 5-aza-2'-deoxycytidine by human cytidine deaminase," *Cancer Chemother. Pharmacol.*,.30:7-11, 1992.

Lowrey and Nienhuis, "Brief Report: Treatment with Azacitidine of Patients with End-Stage β-Thalassemia," *New England Journal of Medicine*, 329(12):845-848, Sep. 16, 1993.

Maas and Rich, "Changing genetic information through RNA editing," *BioEssays*, 22:790-802, 2000.

McCormack et al., "Inhibition of cytidine deaminase by 2-oxopyrimidine riboside and related compounds," *Biochemical Pharmacology*, 29:830-832, 1980.

Mekras et al., "Use of 5-Fluorodeoxycytidine and Tetrahydrouridine to Exploit High Levels of Deoxycytidylate Deaminase in Tumors to Achieve DNA-and Target-directed Therapies," *Cancer Res.*, 44:2551-2560, Jun. 1984.

Olek et al., "A modified and improved method of bisulphate based cytosine methylation analysis," *Nuc. Acids Res.*, 24(24):5064-5066, 1996.

Razin, "CpG methylation, chromatin structure and gene silencing—a three-way connection," *The EMBO Journal*, 17(17):4905-4908, 1998.

Roberts and Selker, "Mutations affecting the biosynthesis of S-adenosylmethionine cause reduction of DNA methylation in *Neurospora crassa*," *Nuc. Acids Res.*, 23(23):4818-4826, 1995.

Rountree and Selker, "DNA methylation inhibits elongation but not initiation of transcription in *Neurospora crassa*," *Genes & Devel.*, 11:2383-2395, 1997.

Sachs et al., "Expression of herpes virus thymidine kinase in *Neurospora crassa*," *Nuc. Acids Res.*, 25(12):2389-2395, 1997.

Sadri and Hornsby, "Rapid analysis of DNA methylation using new restriction enzyme sites created by bisulfite modification," *Nuc. Acids Res.*, 24(24):5058-5059, 1996.

Selker et al, "Dense Nonsymmetrical DNA Methylation Resulting from Repeat-Induced Point Mutation in *Neurospora*," *Science*, 262:1724-1728, Dec. 10, 1993.

Selker, "DNA methylation and chromatin structure: a view from below," *Trends in Biochem. Sci.* (reprint), 15(3)103-107, Mar. 1990.

Selker, et al., "DNA methylation at asymmetric sites is associated with numerous transition mutations," *Proc. Natl. Acad. Sci. USA*, 82:8114-8118, Dec. 1985.

Selker and Garrett, "DNA sequence duplications trigger gene inactivation in *Neurospora crassa*," *Proc. Natl. Acad. Sci. USA*, 85:6870-6874, Sep. 1998.

Selker, "Gene Silencing: Repeats that Count," *Cell*, 97:157-160, Apr. 16, 1999.

Selker, "A Portable Signal Causing Faithful DNA Methylation de Novo in *Neurospora crassa*," *Science*, 238:48-53, Oct. 2, 1987.

Selker et al., "Rearrangement of Duplicated DNA in Specialized Cells of *Neurospora*," *Cell*, 51:741-752, Dec. 4, 1987.

Selker, "Trichostatin A causes selective loss of DNA methylation in *Neurospora*," *Proc. Natl. Acad. Sci. USA*, 95:9430-9435, Aug. 1998.

Shemer et al., "Dynamic methylation adjustment and counting as part of imprinting mechanisms," *Proc. Natl. Acad. Sci. USA*, 93:6371-6376, Jun. 1996.

Shen et al., "Increased Uridine Kinase (ATP: Uridine 5'-Phosphotransferase; EC 2.7.1.48) Activity in Human and Rat Tumors," *Cancer Biochem. Biophys.*, 16:1-15, 1998.

Singer et al., "DNA Methylation Associated with Repeat-Induced Point Mutation in *Neurospora crassa*," *Mol. & Cell. Biology*, 15(10):5586-5597, Oct. 1995.

Soengas et al., "Inactivation of the apoptosis effector *APaf-1* in malignant melanoma," *Nature*, 409:207-211, Jan. 11, 2001.

Taylor et al., "Determination of the order of substrate addition to *Msp*I DNA methyltransferase using a novel mechanism-based inhibitor," *Biochem. J.*, 291:493-504, 1993.

Wang et al., "Use of Oligodexyribonucleotides with Conformationally Constrained Abasic Sugar Targets to Probe the Mechanism of Base Flipping by H*ha*I DNA (Cytosine C5)-methyltransferase," *J. Am. Chem. Soc.*, 122:12422-12434, 2000.

Warnecke et al. "Detection and measurement of PCR bias in quantitative methylation analysis of bisulphate-treated DNA," *Nuc. Acids Res.*, 25(21):4422-4426, 1997.

Xiang et al., "Cytidine Deaminase Complexed to 3-Deazacytidine: A "Valence Buffer" in Zinc Enzyme Catalysis," *Biochemistry*, 35(5):1335-1341, Feb. 6, 1996.

Xiong and Laird, "COBRA: a sensitive and quantitative DNA methylation assay," *Nuc. Acids Res.*, 25(12):2532-2534, 1997.

Cheng et al., "Continuous Zebularine Treatment Effectively Sustains Demethylation in Human Bladder Cance Cells," *Molecular and Cellular Biology*, 24(3):1270-1278 (Feb. 2004).

Cheng et al., "Inhibition of DNA Methylation and Reactivation of Silenced Genes by Zebularine," *Journal of the National Cancer Institute*, 95(5):399-409 (Mar. 2003).

Droz and Culine, "New Prospects for the Treatment of Germ-cell tumours," *Expert Opinion on Investigational Drugs*, 7(7):1139-1157 (1998).

Egger et al., "Epigenetics in human disease and prospects for epigenetic therapy," *Nature*, 429:457-463 (May 2004).

Foubister, "Drug reactivates genes to inhibit cancer," downloaded from http://www.vaccinationnews.com/DailyNews/2003/May/21/DrugReactivates21.htm on Oct. 6, 2004, 3 pp.

Marquez et al., "Potent Inhibition of *Hha*I DNA Methylase by the Aglycon of 2-(1*H*)-Pyrimidinone Riboside (Zebularine) at the G CGC Recognition Domain," *Ann. N.Y. Acad. Sci.*, 1002:154-164 (2003).

Santini et al., "Changes in DNA Methylation in Neoplasia: Pathophysiology and Therapeutic Implications," *Annals of Internal Medicine*, 134(7):573-586 (Apr. 2001).

"Zebularine (NSC 309132)," 8 pp. (Jul. 25, 2005).

Ben-Kasus et al., "Metabolic activation of zebularine, a novel DNA methylation inhibitor, in human bladder carcinoma cells," *Biochemical Pharmacology*, 70:121-133, (2005).

Osterman et al., "5-Fluorocytosine in DNA is a mechanism-based inhibitor of HhaI methylase," *Biochemistry*, 27(14):5204-10 (Jul. 12, 1988).

Supplementary European Search Report from European Patent Application No. 02756825.2 (mailed Feb. 4, 2009).

Liu et al., "Cyclic Urea Nucleosides, Cytidine Deaminase Activity as a Function of Aglycon Ring Size," *J. Med. Chem.* 24(6):662-666, 1981.

Zhou et al., "Zebularine: A Novel DNA Methylation Inhibitor that Forms a Covalent Complex with DNA Methyltransferases," *J. Mol. Biol.* 321(4):591-599, Aug. 23, 2002.

Maehara et al., "Activity of Various Enzymes of Pyrimidine Nucleotide and DNA Synthesis in Normal and Neoplastic Human Tissues," *Gann* 73(2): 289-298, Apr. 1982.

\* cited by examiner

Cytidine      5-Azacytidine      Zebularine
(5-Aza-CR)      (Zeb)

Induction of myotubules in C3H 10T1/2 C18 cells

P16 locus studied by Ms-SNuPE

P3 locus studied by Ms-SNuPE

5'-TGTCA<u>GXG</u>CATGG-3' (XP)
3'-ACAGT<u>CGMG</u>TACC-5' (B'M6)
X = 2(1H)pyrimidinone
M = 5-Methylcytosine
5'-TGTCA<u>GZG</u>CATGG-3' (BZ7)
3'-ACAGT<u>CGMG</u>TACC-5' (B'M6)
Z = 5-Azacytosine The substrate ODN used was:

SEQUENCE LISTING

<160> NUMBER OF SEQ ID NOS: 23

<210> SEQ ID NO 1
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 1
agccttcggc tgactggctg g                                            21

<210> SEQ ID NO 2
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 2
ctgcccatca tcatgacctg ga                                           22

```
<210> SEQ ID NO 3
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 3
cagccgagcc acatcgctca gaca                                          24

<210> SEQ ID NO 4
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 4
tgaggctgtt gtcatacttc tc                                            22

<210> SEQ ID NO 5
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 5
gtaggtgggg aggagtttag tt                                            22

<210> SEQ ID NO 6
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 6
tctaataacc aaccaacccc tcct                                          24

<210> SEQ ID NO 7
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 7
ttgattattt tgttttttttt ggtaggtt                                     28

<210> SEQ ID NO 8
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 8
caaattctca aatcatcaat cctcacct                                      28

<210> SEQ ID NO 9
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 9
```

```
gtttataggt ttagaggttt t                                          21

<210> SEQ ID NO 10
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 10
aacacataaa cctatttaa actta                                       25

<210> SEQ ID NO 11
<211> LENGTH: 15
<212> TYPE: DNA
<213> ORGANISM: Artificial sequence
<220> FEATURE:
<223> OTHER INFORMATION: synthetic oligonucleotide

<400> SEQUENCE: 11
tttgagggat agggt                                                 15

<210> SEQ ID NO 12
<211> LENGTH: 18
<212> TYPE: DNA
<213> ORGANISM: Artificial sequence
<220> FEATURE:
<223> OTHER INFORMATION: synthetic oligonucleotide

<400> SEQUENCE: 12
ttttaggggt gttatatt                                              18

<210> SEQ ID NO 13
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 13
tttttttgtt tggaaagata t                                          21

<210> SEQ ID NO 14
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 14
gttggtggtg ttgtat                                                16

<210> SEQ ID NO 15
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 15
aggttatgat gggtag                                                16

<210> SEQ ID NO 16
<211> LENGTH: 22
<212> TYPE: DNA
<213> ORGANISM: Artificial sequence
```

```
<220> FEATURE:
<223> OTHER INFORMATION: synthetic oligonucleotide

<400> SEQUENCE: 16
tattagaggt agtaattatg tt                                              22

<210> SEQ ID NO 17
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 17
ggtatagttt gagtat                                                     16

<210> SEQ ID NO 18
<211> LENGTH: 21
<212> TYPE: DNA
<213> ORGANISM: Artificial sequence
<220> FEATURE:
<223> OTHER INFORMATION: synthetic oligonucleotide

<400> SEQUENCE: 18
ttttatttat tgttattatg g                                               21

<210> SEQ ID NO 19
<211> LENGTH: 26
<212> TYPE: DNA
<213> ORGANISM: Artificial sequence
<220> FEATURE:
<223> OTHER INFORMATION: synthetic oligonucleotide

<400> SEQUENCE: 19
tattttttaa tagtattatt ttttat                                          26

<210> SEQ ID NO 20
<211> LENGTH: 13
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (7)..(7)
<223> OTHER INFORMATION: n = 2'-deoxy-zebularine or 2'-deoxy-5-
      azacytidine

<400> SEQUENCE: 20
tgtcagngca tgg                                                        13

<210> SEQ ID NO 21
<211> LENGTH: 13
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n = 5-methylcytidine

<400> SEQUENCE: 21
acagtcgngt acc                                                        13

<210> SEQ ID NO 22
<211> LENGTH: 24
<212> TYPE: DNA
```

```
<213> ORGANISM: Artificial sequence
<220> FEATURE:
<223> OTHER INFORMATION: synthetic oligonucleotide

<400> SEQUENCE: 22
gatcgcggat tcggaatgcg caat                                      24

<210> SEQ ID NO 23
<211> LENGTH: 24
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (20)..(20)
<223> OTHER INFORMATION: n = 5-Methylcytosine

<400> SEQUENCE: 23
ctagcgccta agccttacgn gtta                                      24
```

INHIBITOR OF DNA METHYLATION

REFERENCE TO RELATED APPLICATIONS

This is the U.S. National Stage of International Application No. PCT/US02/24223, filed Jul. 30, 2002, (published in English under PCT Article 21(2)), which in turn claims the benefit of U.S. Provisional Application No. 60/309,242, filed Jul. 31, 2001, and U.S. Provisional Application No. 60/311,435, filed Aug. 10, 2001. These applications are incorporated herein in their entirety.

STATEMENT OF GOVERNMENT SUPPORT

This invention was made with government support under Grant Nos. GM35690 and CA82422 awarded by the National Institutes of Health. The government has certain rights in the invention. The government also may have certain rights in the invention due to at least one inventor's employment by the National Institutes of Health.

FIELD OF THE DISCLOSURE

This disclosure relates to methods of inhibiting DNA methylation and methods of treating or ameliorating hypermethylation-related disease, using the compound Zebularine and related compounds.

BACKGROUND

DNA methyltransferases (also referred to as DNA methylases) transfer methyl groups from the universal methyl donor S-adenosyl methionine to specific sites on a DNA molecule. Several biological functions have been attributed to the methylated bases in DNA. The most established biological function is the protection of the DNA from digestion by cognate restriction enzymes. The restriction modification phenomenon has been observed only in bacteria. Mammalian cells possess at least several methyltransferases; one of these (DNMT1) preferentially methylates cytosine residues on the DNA, which are 5' (upstream) neighbors of guanine (forming the dinucleotide CpG). This methylation has been shown by several lines of evidence to play a role in gene activity, cell differentiation, tumorigenesis, X-chromosome inactivation, genomic imprinting and other major biological processes (Razin and Riggs, eds. in *DNA Methylation Biochemistry and Biological Significance*, Springer-Verlag, New York, 1984).

When most gene sequences contain many methylated cytosines, they are less likely to be expressed (Willson, *Trends Genet.* 7:107-109, 1991); in particular, if a site in the promoter of the gene is methylated, gene silencing is likely to occur. Hence, if a maternally-inherited copy of a gene is more highly methylated than the paternally-inherited copy, the paternally-inherited copy will be expressed more effectively. Similarly, when a gene is expressed in a tissue-specific manner, that gene often will be unmethylated in the tissues where it is active but highly methylated in the tissues where it is inactive.

Incorrect methylation is believed to be the cause of some diseases such as Beckwith-Wiedemann syndrome and Prader-Willi syndrome (Henry et al., *Nature* 351:665, 1991; Nicholls et al., *Nature* 342:281, 1989), as well as a contributing factor in many cancers (Laird and Jaenisch, *Hum. Mo. Genet.* 3 Spec. No.: 1487-1495, 1994). Expression of a tumor suppressor gene can be abolished by de novo DNA methylation of a normally unmethylated 5' CpG island (Issa et al., *Nature Genet.*, 7:536, 1994; Herman et al., *Proc. Natl. Acad. Sci., U.S.A.*, 91:9700, 1994; Merlo et al., *Nature Med.*, 1:686, 1995; Herman et al., *Cancer Res.*, 56:722, 1996; Graff et al., *Cancer Res.*, 55:5195, 1995; Herman et al., *Cancer Res.*, 55:4525, 1995). Such hypermethylation has now been associated with the loss of expression of VHL, a renal cancer tumor suppressor gene on 3p (Herman et al., *Proc. Natl. Acad. Sci. USA*, 91:9700-9704, 1994), the estrogen receptor gene on 6q (Ottaviano et al., *Cancer Res.*, 54:2552, 1994) and the H19 gene on 11p (Steenman et al., *Nature Genetics*, 7:433, 1994). Similarly, a CpG island has been identified at 17p 13.3, which is aberrantly hypermethylated in multiple common types of human cancers (Makos et al., *Proc. Natl. Acad. Sci. USA*, 89:1929, 1992; Makos et al., *Cancer Res.*, 53:2715, 1993; Makos et al., *Cancer Res.* 53:2719, 1993). This hypermethylation coincides with the timing and frequency of 17p losses and p53 mutations in brain, colon, and renal cancers. Many effects of methylation are discussed in detail for instance in published International patent application PCT/US00/02530.

Both 5-fluorodeoxycytidine (FdCyd) and 5-azacytidine (5-aza-CR) have been shown to inhibit methylation of DNA with resultant effects on gene expression and cell differentiation (Jones and Taylor, *Cell* 20:85-93, 1980; Osterman et al., *Biochemistry* 27:5204-5210, 1988). However, these compounds are unstable or produce toxic metabolites in vivo (Santi et al., *Proc. Natl. Acad. Sci. USA* 91:6993-6997, 1984; Newman et al., *Proc. Natl. Acad. Sci. USA* 79:6419-6423, 1982). Thus, there exists a need for an effective, stable, and low-toxicity inhibitor of DNA methylation.

SUMMARY

It has now been discovered that Zebularine is a potent inhibitor of methylation, and that it can specifically reactivate silenced tumor suppressor genes. Zebularine can be used to inhibit methylation and thereby combat certain diseases (including cancers that have been linked to hypermethylation) and activate methylation-silenced genes in plants, fungi, and animals. Substantially more stable than 5-azacytidine, Zebularine can be given orally, which is tremendously beneficial in the clinical setting.

This disclosure provides methods of employing the hypomethylating activity of Zebularine (and derivatives, analogs, and mimetics), for instance to reduce or reverse DNA methylation, to inhibit, ameliorate, reverse, reduce or relieve methylation-linked diseases, conditions, and disorders, and to ameliorate or reduce a tumorigenic state of a tumor. The disclosure further provides kits for use in these methods. Also provided are DNA and RNA oligonucleotides comprising Zebularine, 2'-deoxy-Zebularine and derivatives thereof; and pharmaceutical preparations comprising Zebularine and Zebularine derivatives.

The foregoing and other features and advantages will become more apparent from the following detailed description of several embodiments, which proceeds with reference to the accompanying figures.

The ramp symbols at the top of the figure represent increasing concentrations of drug. Drug concentrations were 12 and 24 µM 5-AC; 0.33 and 3.3 µM TSA; and 20, 39, 78, 160 and 310 µM Zebularine. The positions of selected size standards (kb) are indicated.

Figure 5:
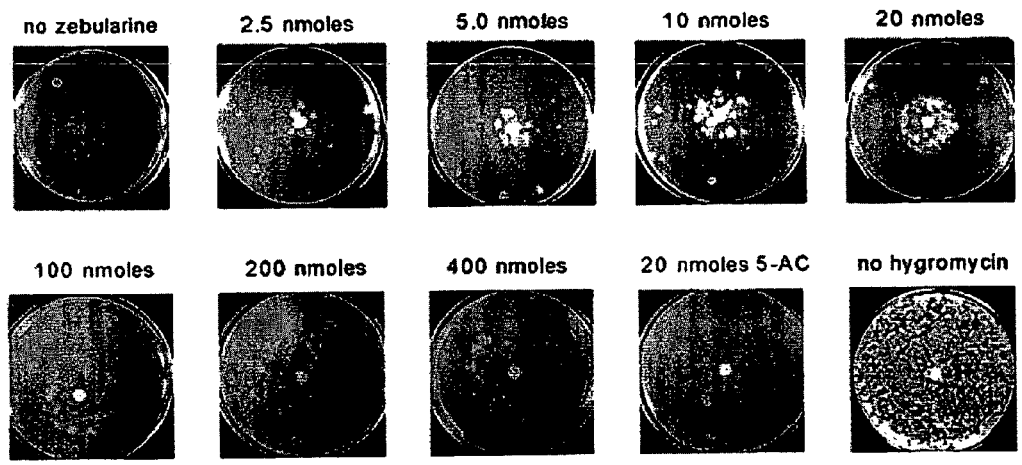

FIG. 5 is a series of photographs of plate assays, showing reactivation of the silenced hph gene in *Neurospora crassa* by Zebularine. *N. crassa* strain N644 has a single copy of the *E. coli* hph gene that was silenced by cytosine methylation. The active hph gene confers hygromycin resistance.

Treatments are indicated above each plate; the listed compound was applied to the paper discs in the middle of each plate. With the exception of the "no hygromycin" plate, all plates had 5 mg hygromycin B added in a 5 ml 0.7% agar overlay after 24 hours growth at 32° C. The plates were then incubated an additional two days at the same temperature and photographed.

Figure 6:
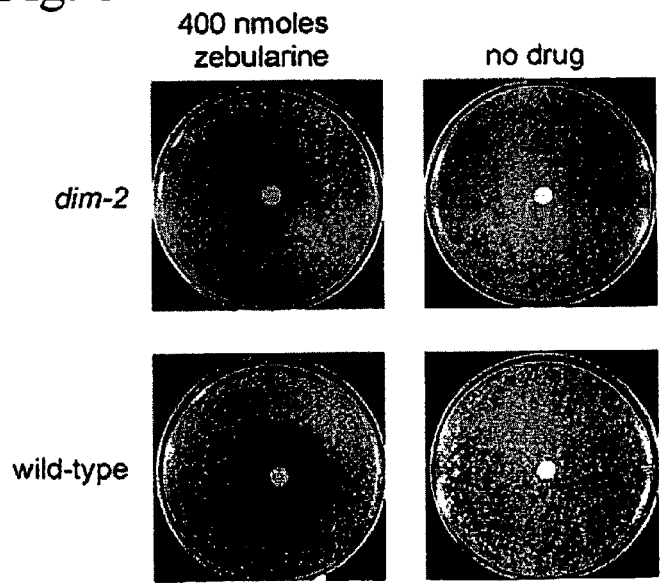

FIG. 6 is a series of photographs of plate assays, illustrating that the inhibitory growth effects of Zebularine on *N. crassa* do not depend on the dim-2 DNA methyltransferase.

Strains with mutations in dim-2 lack all detectable methyltransferase activity. A dim-2 strain (N613) and a wild-type control (N242) were challenged with a high concentration of Zebularine. The concentration of Zebularine is indicated above the plates and was applied to the paper disc as in FIG. 5; no hygromycin was applied to these plates.

Figure 7:
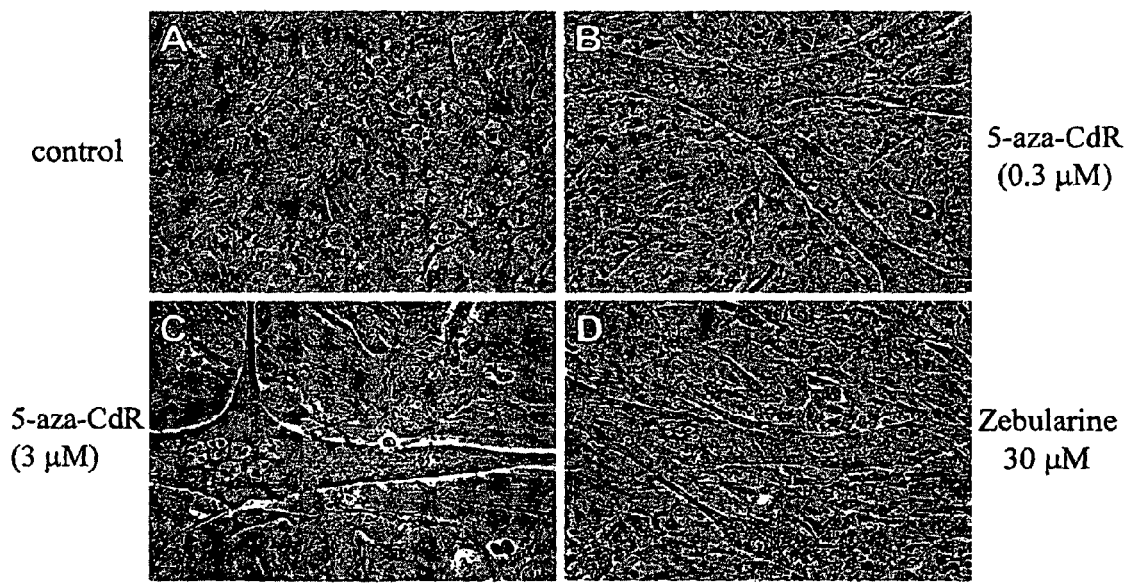

FIG. 7 is a series of four phase contrast micrographs of muscle formation in mouse 10T1/2 cells after the indicated treatments.

Figure 8:
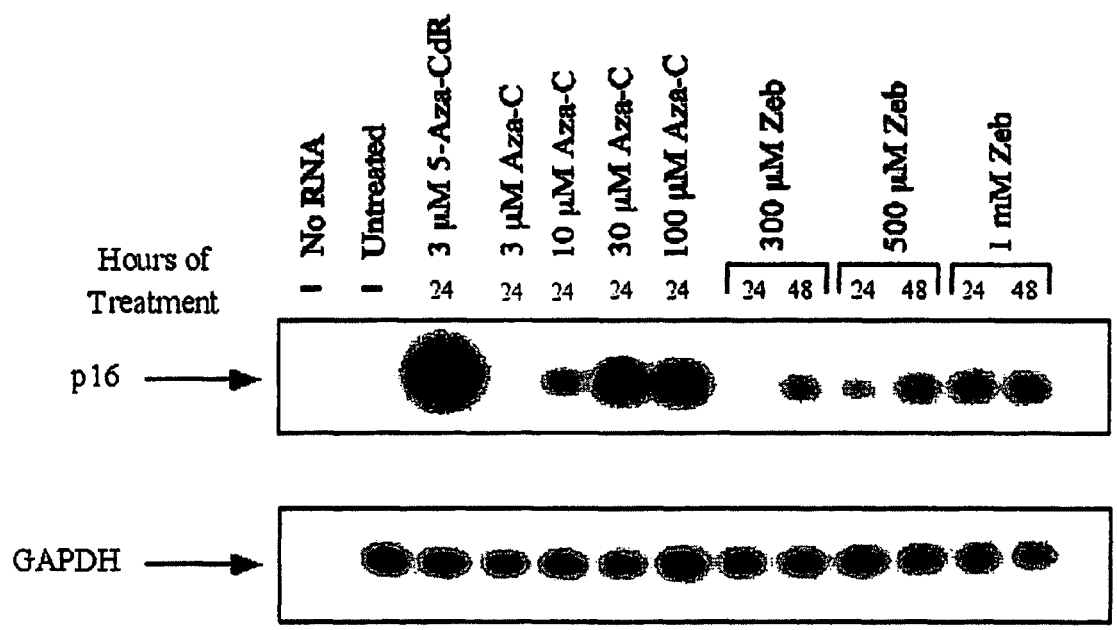

FIG. 8 is a RT-PCR analysis, showing the level of p16 mRNA produced in human T24 cells subjected to the indicated treatments. Parallel GAPDH mRNA levels are also shown; transcription of GAPDH is essentially unaffected by methylation.

Figure 9A:
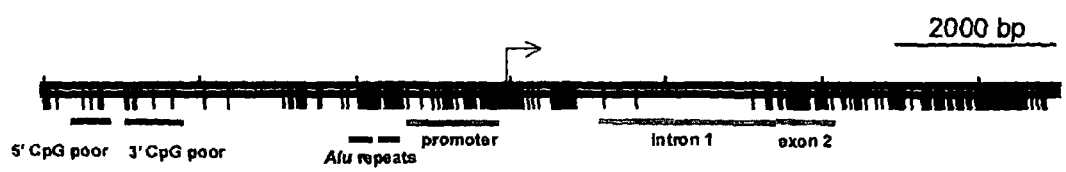
Figure 9B:
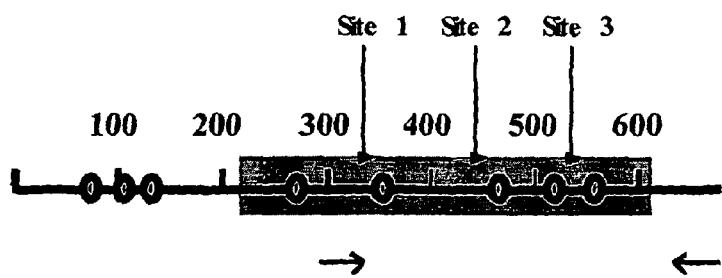

FIG. 9 schematically illustrates the p16 (FIG. 9A) and p3 (FIG. 9B) loci used for Ms-SNuPE methylation studies.

Figure 10A:
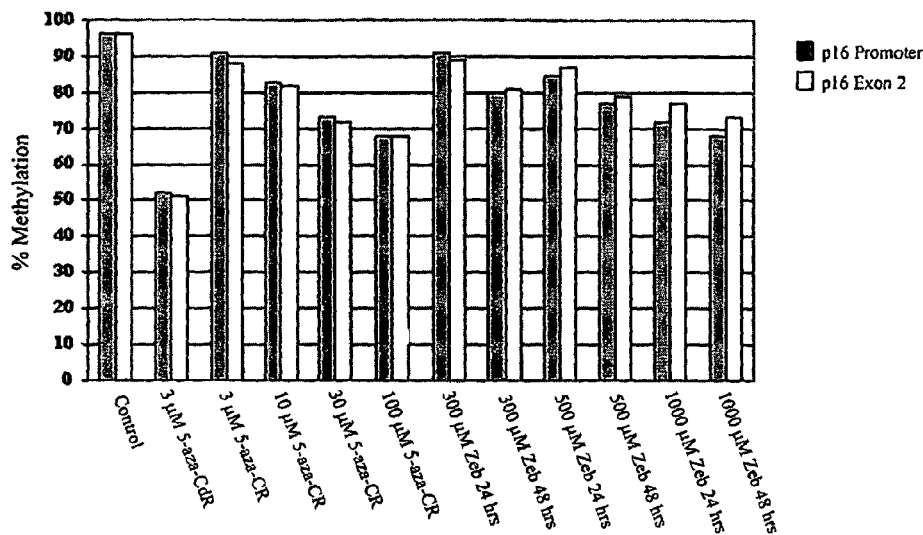
Figure 10B:
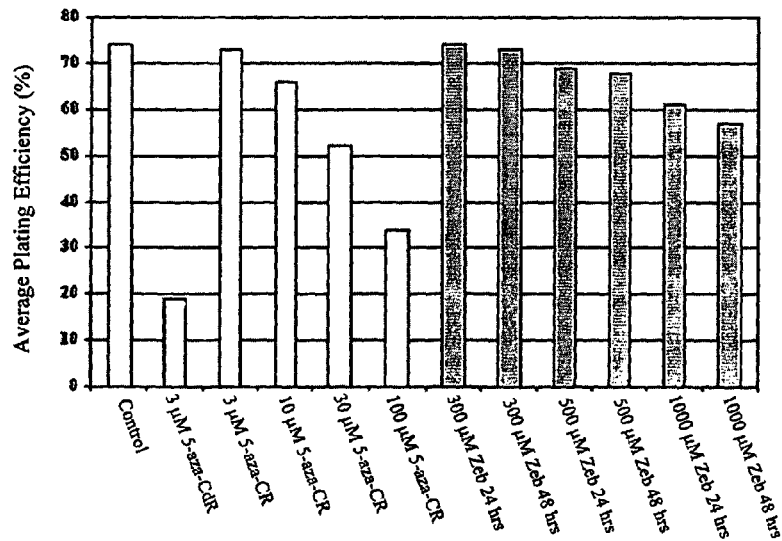

FIG. 10 is a pair of bar graphs showing methylation status in T24 cells of p16 promoter and exon 2 (FIG. 10A) and the corresponding level of toxicity (FIG. 10B) for the indicated treatments. Drug treatments are indicated below each bar.

Figure 11A:
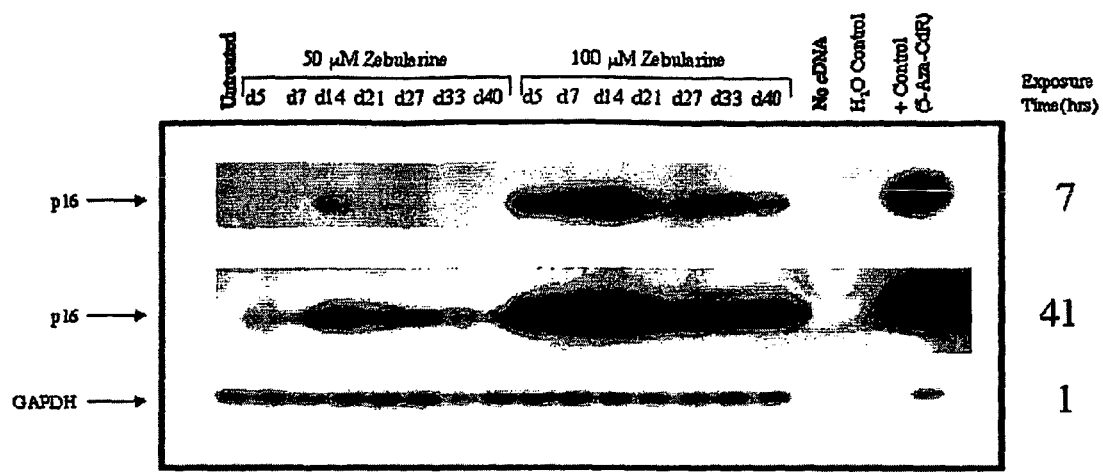

FIG. 11 illustrates an analysis of the effects of long-term, continuous treatment of T24 cells with Zebularine. FIG. 11A is a RT-PCR analysis, showing the level of p16 gene expression in T24 cells treated with either 50 µM or 100 µM of Zebularine for the indicated time points; two film exposure times (7 and 41 hours) are shown. As in FIG. 8, parallel GAPDH levels are shown for comparison.

Figure 11B:
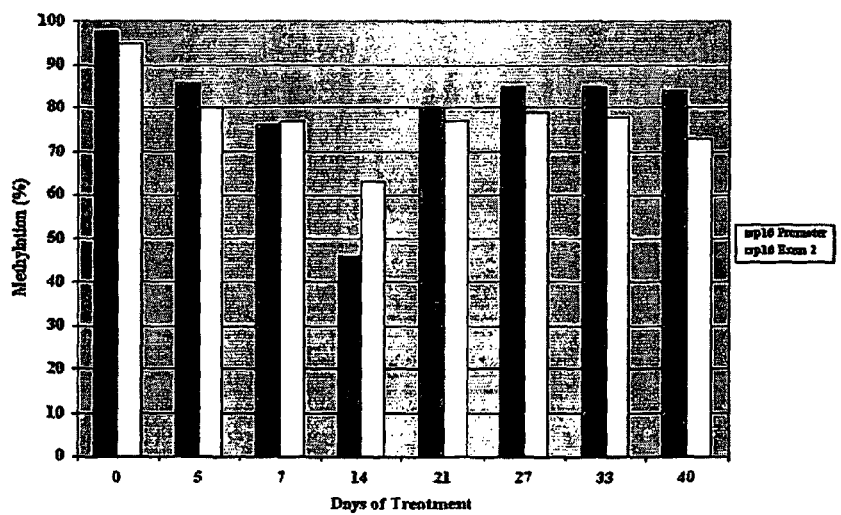

FIG. 11B shows a quantitative summary of the levels of p16 promoter and p16 exon 2 methylation in T24 cells treated with the 100 µM Zebularine for the indicated times. The maximum demethylation observed after treatment with 100 µM Zebularine (from ~96% to ~47%) occurs at Day 14.

Figure 12:
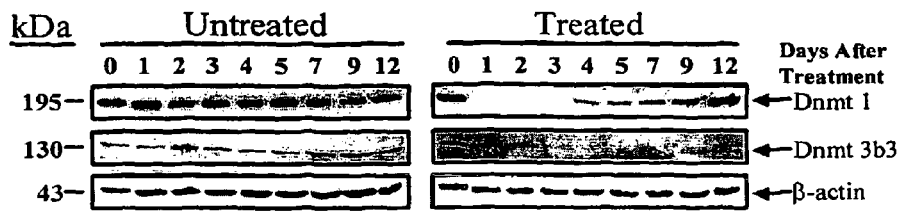

FIG. 12 shows Western blot analyses detecting levels of DNMT1 and DNMT3b3 for cells treated with Zebularine and untreated cells.

Figure 13:
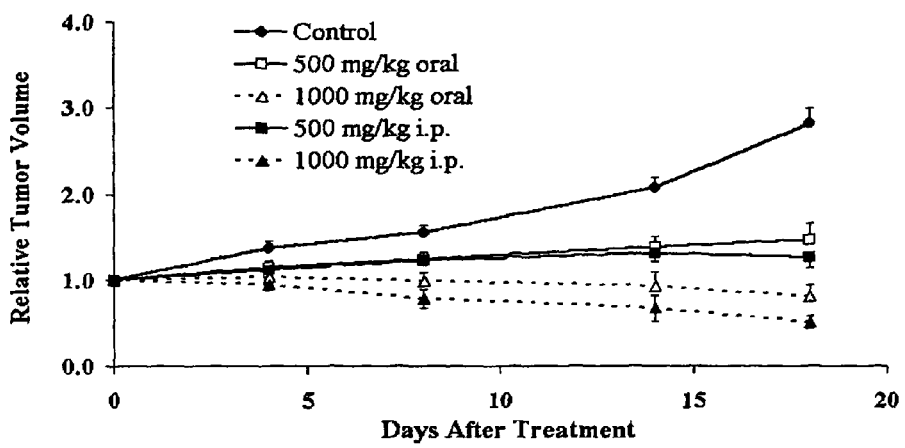

FIG. 13 is a graph of relative tumor volume vs. time for BALB/c nu/nu mice treated with Zebularine, showing suppression of tumor growth in treated groups.

Figure 14:
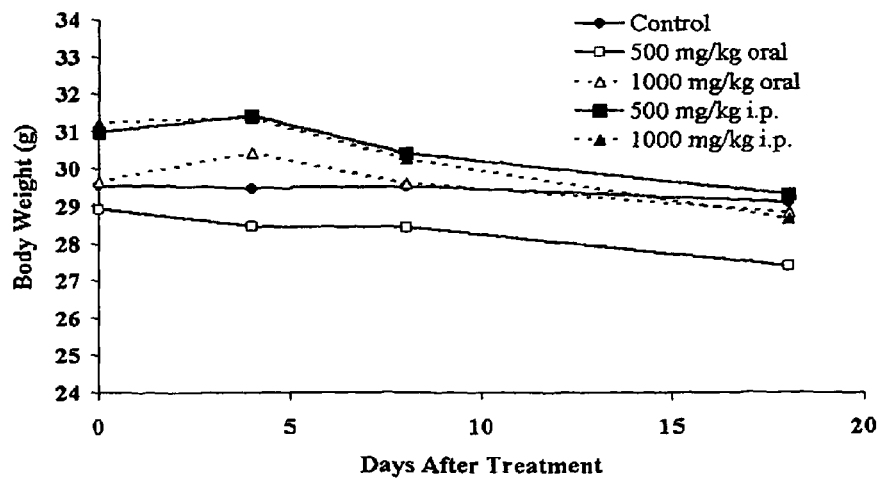

FIG. 14 is a graph of body weight vs. time for BALB/c nu/nu mice treated with Zebularine, showing minimal weight loss for all treated groups.

Figure 15:
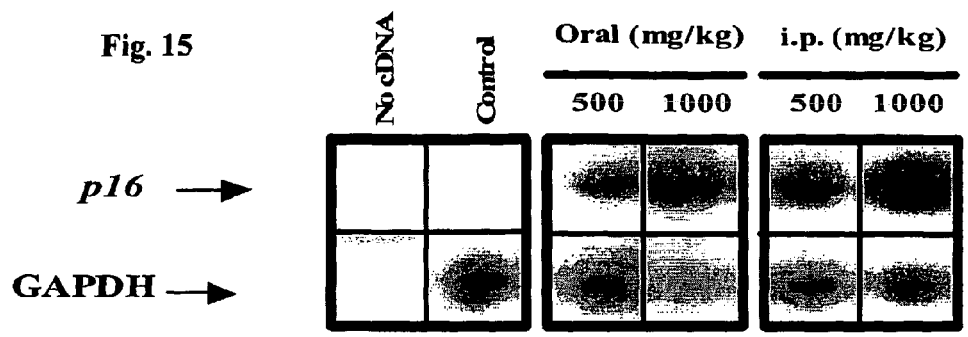

FIG. 15 shows reactivation of p16 gene expression in T24 cells by the indicated drugs.

Figure 16:
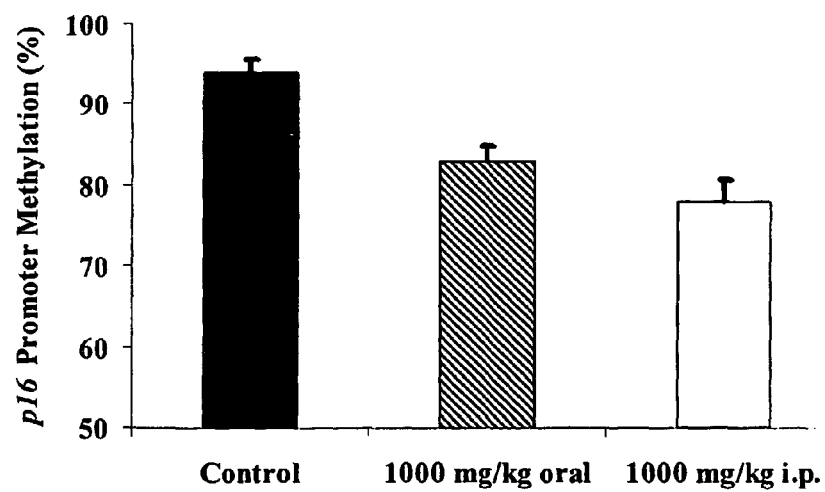

FIG. 16 is a bar graph depicting the relative levels of p16 promoter methylation for the indicated groups.

Figure 17:
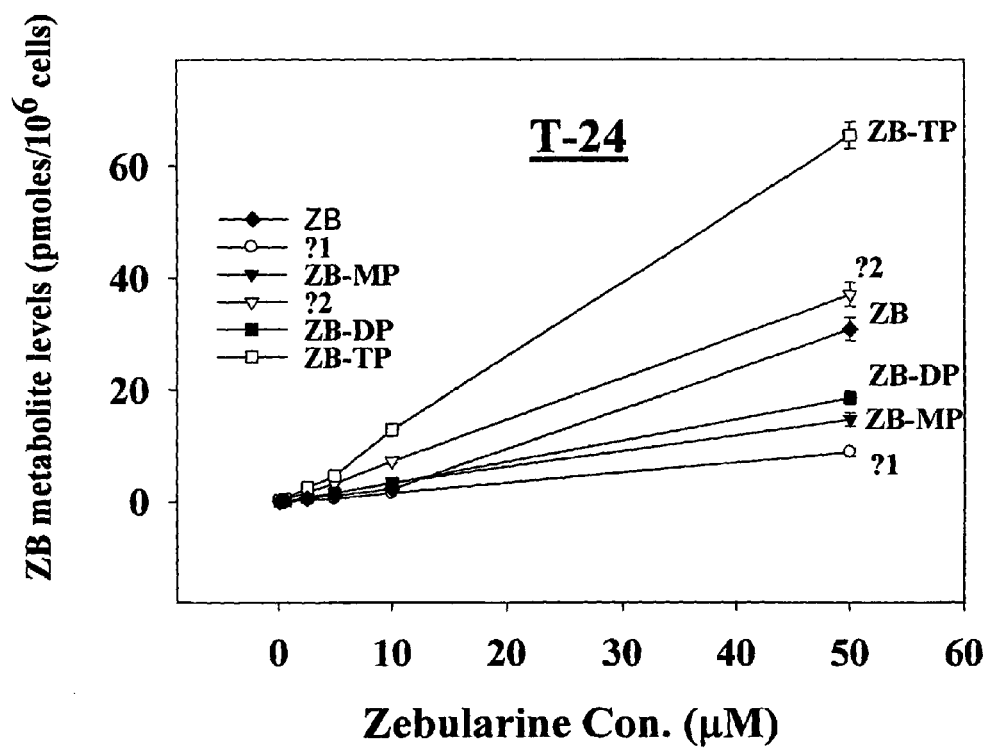

FIG. 17 shows a dose-dependent increase in Zebularine metabolites (pmoles/$10^6$ cells) in T24 cells after a 6 hr incubation period (10 µM, 1 µCi). ZB, ZB-MP, ZB-DP and ZB-TP correspond, respectively, to Zebularine, 5'-mono, 5'-di- and 5'-triphosphate metabolites. There are two unidentified metabolites, indicated by the symbols ?1 and ?2.

Figure 18:
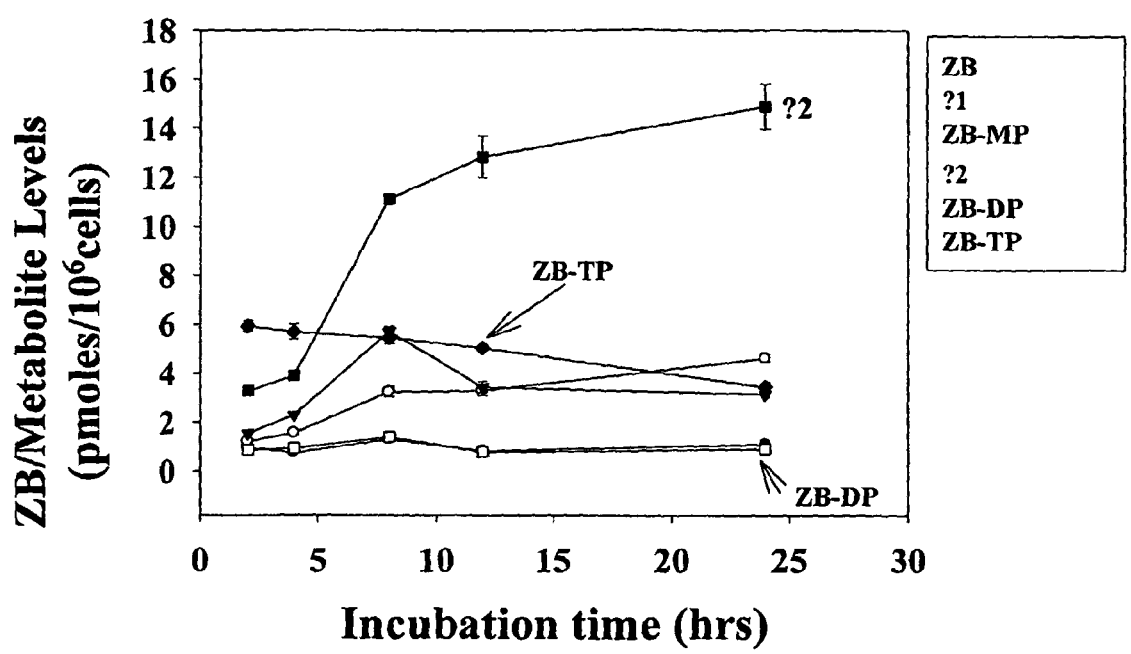

FIG. 18 shows a time course of metabolite levels in T24 cells after a 24 hr incubation period with Zebularine (ZB, 10 µM, 1 µCi).

Figure 19:
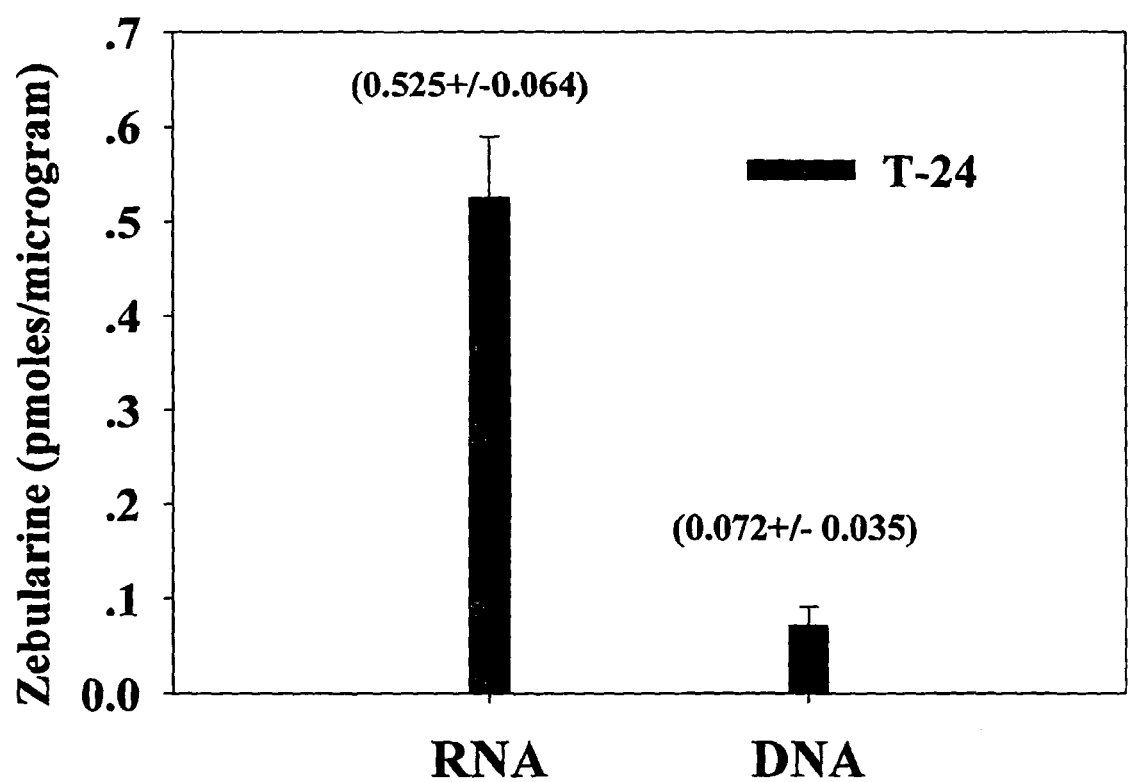

FIG. 19 is a bar graph depicting the relative incorporation of Zebularine into DNA and RNA in T24 cells, showing that approximately 7 times the amount of Zebularine is incorporated into RNA as DNA.

Figure 20:
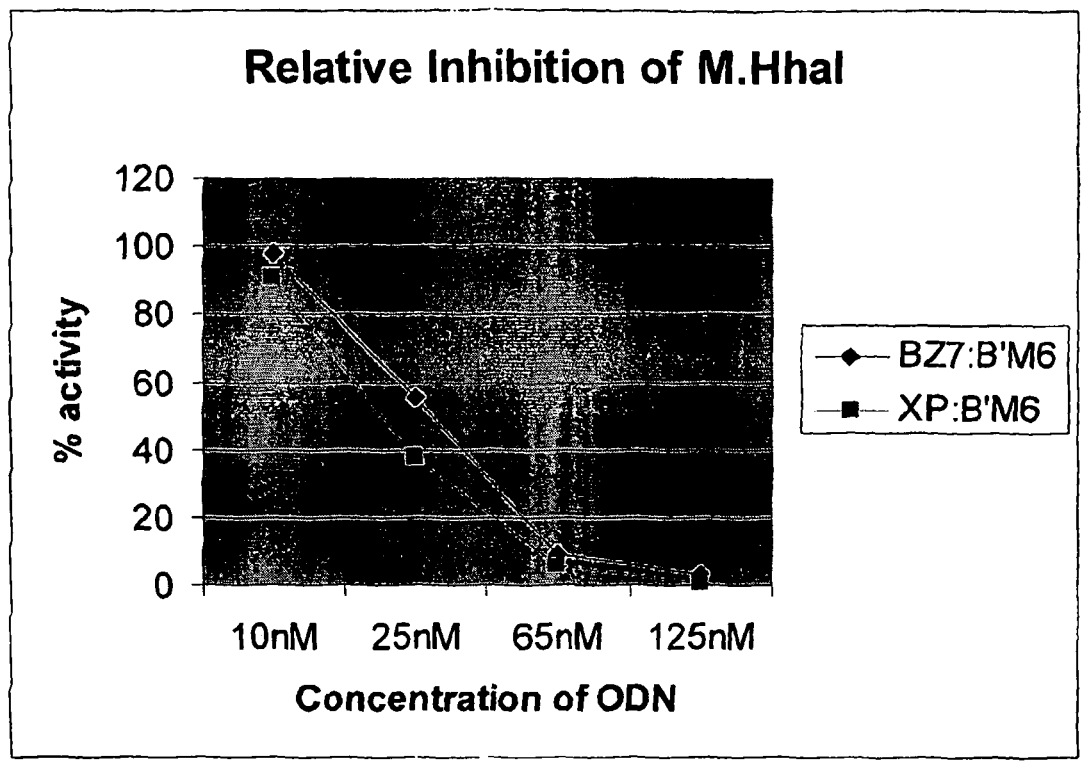

FIG. 20 is a graph showing the relative inhibition of HhaI methyltransferase by oligonucleotides including either a 2'-deoxy-Zebularine or a 2'-deoxy-5-azacytidine.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1: is a p16 sense cDNA amplification primer.
SEQ ID NO: 2: is a p16 antisense cDNA amplification primer.
SEQ ID NO: 3: is a GAPDH sense cDNA amplification primer.
SEQ ID NO: 4: is a GAPDH antisense cDNA amplification primer.
SEQ ID NO: 5: is a p16 promoter/exon 1 sense primer for bisulfite-treated DNA amplification.
SEQ ID NO: 6: is a p16 promoter/exon 1 antisense primer for bisulfite-treated DNA amplification.
SEQ ID NO: 7: is a p16 exon 2 sense primer for bisulfite-treated DNA amplification.
SEQ ID NO: 8: is a p16 exon 2 antisense primer for bisulfite-treated DNA amplification.
SEQ ID NO: 9: is a P3 sense primer for bisulfite-treated DNA amplification
SEQ ID NO: 10: is a P3 antisense primer for bisulfite-treated DNA amplification.
SEQ ID NOS: 11, 12, and 13 are p16 promoter/exon 1 SNuPE primers.
SEQ ID NOs: 14, 15, and 16 are p16 exon 2 SNuPE primers.
SEQ ID NOs: 17, 18, and 19 are p3 SNuPE primers.
SEQ ID NO: 20 is a Zebularine-derivatized oligonucleotide, where N re presents 2'-deoxy-Zebularine.
SEQ ID NO: 21 is complementary to SEQ ID NO: 20 and has a 5-methyl cytosine at position 6 from the 5' end.
SEQ ID NO: 22 is a methylation substrate oligonucleotide.
SEQ ID NO: 23 complementary to SEQ ID NO: 22 and has a 5-methyl cytosine at position 5 from the 5' end.

DETAILED DESCRIPTION

I. Abbreviations 5-aza-CR (also 5-azaC, 5-AC): 5-azacytidine
5-aza-CdR: 5-aza-2'-deoxycytidine
CK: cytidine kinase
FdCyd: 5-fluorodeoxycytidine
GM-CSF: granulocyte macrophage colony stimulating factor
GST: glutathione-S-transferase
IL-2: Interleukin 2
QSAR: quantitative structure activity relationships
RE: restriction endonuclease
TNF: tumor necrosis factor
TSA: trichostatin A
UK: uridine kinase
Zeb: Zebularine

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Chemistry terms herein, for which specific explanations are not noted, are used according to conventional usage in the art, as exemplified by *The McGraw-Hill Dictionary of Chemical Terms* (1985) and *The Condensed Chemical Dictionary* (1981).

In order to facilitate review of the various embodiments of the disclosure, the following explanations of specific terms are provided:

Alcohol: This term refers to a chemical compound with the structure R—OH, wherein R is alkyl, especially lower alkyl (for example in methyl, ethyl or propyl alcohol). An alcohol may be either linear or branched, such as isopropyl alcohol.

Alkyl: The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to five carbon atoms. This term is further exemplified by such radicals as methyl, ethyl, n-propyl, i-propyl, n-butyl, t-butyl, i-butyl (or 2-methylpropyl), cyclopropylmethyl, i-amyl, and n-amyl. Lower alkyl groups can also be unsubstituted or substituted, where a specific example of a substituted alkyl is 1,1-dimethyl propyl.

Alkoxy: The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent.

Amino: The term "amino" refers to a chemical functionality —NR1R2 where R1 and R2 are independently hydrogen, alkyl, or aryl groups.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a substance related to a base structure, and theoretically derivable from the base structure. A mimetic is a biomolecule that mimics the activity of another biologically active molecule. Biologically active molecules can include chemical structures that mimic the biological activities of a compound, for instance Zebularine.

Animal: Living multi-cellular organisms, for instance a vertebrate (a category that includes, for example, mammals, and birds). The term mammal includes both human and non-human mammals. Similarly, the term "subject" includes both human and veterinary subjects.

Anti-proliferative activity: An activity of a molecule, e.g., a compound, which reduces proliferation of at least one cell type, but which may reduce the proliferation (either in absolute terms or in rate terms) of multiple different cell types (e.g., different cell lines, different species, etc.). In specific embodiments, an anti-proliferative activity will be apparent against cells (either in vitro or in vivo) that exhibit a hyperproliferative condition, such as is characteristic of certain disorders or diseases.

In certain embodiments, an anti-proliferative activity can be an anti-tumor or anti-neoplastic activity of a compound. Such molecules will be useful to inhibit or prevent or reduce cellular proliferation or growth, e.g., in a tumor, such as a malignant neoplasm.

Aryl: The term "aryl" refers to a monovalent unsaturated aromatic carbocyclic group having a single ring (e.g. phenyl) or multiple condensed rings (e.g. naphthyl or anthryl), which are optionally unsubstituted or substituted with, e.g., halogen, alkyl, alkoxy, mercapto (—SH), alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

Carboxyl: This term refers to the radical —COOH, and substituted carboxyl refers to —COR where R is alkyl, lower alkyl or a carboxylic acid or ester.

DNA (deoxyribonucleic acid): DNA is a long chain polymer which comprises the genetic material of most living organisms (some viruses have genes comprising ribonucleic acid (RNA)).

The units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Halogen: The term "halogen" refers to fluoro, bromo, chloro and iodo substituents.

Heterocycle: The term "heterocycle" refers to a monovalent saturated, unsaturated, or aromatic carbocyclic group having a single ring (eg. benzyl, morpholino, pyridyl or furyl) or multiple condensed rings (e.g. naphthyl, quinolinyl, indolizinyl or benzo[b]thienyl) and having at least one heteroatom, defined as N, O, P, or S, within the ring, which can optionally be unsubstituted or substituted with, e.g. halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

Hydroxyl: This term refers to the chemical group —OH.

Hyper-proliferative disorder: A disorder characterized by abnormal proliferation of cells, and generically includes skin disorders such as psoriasis as well as benign and malignant tumors of all organ systems.

Injectable composition: A pharmaceutically acceptable fluid composition comprising at least one active ingredient, e.g., Zebularine or a compound with Zebularine-like hypomethylation activity. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the compounds and peptides of this disclosure are conventional; formulations are well known in the art.

Methylation: A chemical or biochemical process of introducing a methyl group into an organic molecule. DNA methylation, the addition of a methyl group onto a nucleotide, is a postreplicative covalent modification of DNA that is catalyzed by the DNA methyltransferase enzyme (MeTase) (Koomar et al., *Nucl. Acids Res.* 22:1-10, 1994; and Bestor et al., *J. Mol. Biol.* 203:971-983, 1988).

In biological systems, DNA methylation can serve as a mechanism for changing the structure of DNA without altering its coding function or its sequence. DNA methylation is a heritable, reversible and epigenetic change. It can alter gene expression, particularly by inactivating genes, which has profound developmental and disease consequences.

Methylation of CpG islands that are associated with tumor suppressor genes can cause decreased gene expression. Increased methylation of such regions often leads to reduction of normal gene expression, which may cause the selection of a population of cells having a selective growth advantage and thus are or become malignant.

As used herein, the term "hypermethylation" refers to an increased or high level (above a reference level, such as wild-type or other basal level) of DNA methylation at a specific site on a nucleic acid molecule (e.g., a CpG island), or more generally in a genome or region of a genome (e.g., a promoter region).

As used herein, the term "hypomethylation" refers to a decreased or low level (below a reference level, such as wild-type or other basal level) of DNA methylation at a specific site on a nucleic acid molecule (e.g., a CpG island), or more generally in a genome or region of a genome (e.g., a promoter region).

As used herein, the term "hypomethylating agent" refers to an agent that reduces or reverses DNA methylation, either at a specific site (e.g., a specific CpG island) or generally throughout a genome. Hypomethylating agents can be referred to as possessing "hypomethylating activity." By way of example, such activity is measured by determining the methylation state and/or level of a specific DNA molecule or site therein, or the general methylation state of a cell, on parallel samples that have and have not been treated with the hypomethylating agent (or putative hypomethylation agent). A reduction in methylation in the treated (versus the untreated) sample indicates that the agent has hypomethylating activity.

Different hypomethylating agents, or different treatments with the same agent, or different systems that are treated, or methyltransferase mutants, will yield different levels of methylation reduction. In some embodiments, the methylation level is reduced by at least 5% upon treatment with a hypomethylating agent; in other embodiments it is reduced by at least 10%, by at least 15%, by at least 20%, by at least 25%, by at least 30%, by at least 40%, or by at least 50% compared to an untreated sample. Particularly effective hypomethylating agents, or agents used in particularly susceptible systems, will yield even greater reduction levels, for instance at least 60%, 70%, 80%, 90%, or in some examples 95% or more.

Methylation-mediated condition/disease/disorder: A biological condition, disease or disorder of a subject that is associated with, caused by, or influenced by the methylation state (e.g., the extent of methylation) of a DNA sequence, or level of methylation throughout the genome of the subject.

Hypermethylation-associated diseases, disorders, and conditions are characterized by exhibiting hypermethylation of one or more DNA sequences. Such diseases, disorders, and conditions therefore can be identified by examining the methylation state (or level) of nucleic acids in a subject known to or suspected of suffering therefrom; a high level of specific or general DNA methylation indicates that the disease/disorder/condition is hypermethylation-associated. It is beneficial to treat (or prevent) such diseases, disorders, and conditions with the provided Zebularine-comprising compositions.

Hypomethylation-associated diseases, disorders, and conditions are characterized by exhibiting hypomethylation of one or more DNA sequences. As with hypermethylation, hypomethylation-associated diseases/disorders/conditions can be identified by examining the methylation state (or level) of nucleic acids in the subject known to or suspected of suffering therefrom.

Nucleoside: "Nucleoside" includes, but is not limited to, a monomer that includes a base, such as a pyrimidine, purine, or synthetic analogs thereof, linked to a carbohydrate.

Nucleotide: A nucleotide is a nucleoside plus a phosphate, and forms one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA. Specifically included in the term analog are oligonucleotides that contain one or more Zebularine derivatives integrated into the molecule.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful with the compounds described herein are conventional. See, for instance, *Remington's Pharmaceutical Sciences*, by E. W. Martin, Mack Publishing Co., Easton, Pa., 15th Edition (1975), which describes compositions and formulations suitable for pharmaceutical delivery.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Prodrug: Any molecule that undergoes in vivo metabolic conversion to one or more pharmacologically active compounds.

Tumor: A neoplasm that may be either malignant or non-malignant. "Tumors of the same tissue type" refers to primary tumors originating in a particular organ (such as breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. It is further to be understood that all base sizes or amino acid sizes, and all molecular weight or molecular mass values, given for nucleic acids or polypeptides are approximate, and are provided for description. All chemical compounds include both the (+) and (−) stereoisomers, as well as either the (+) or (−) stereoisomer, unless otherwise specified.

Although methods and materials similar or equivalent to those described herein can be used in the practice or the disclosed methods and compositions, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

This disclosure provides methods of inhibiting a DNA methyltransferase, comprising contacting the DNA methyltransferase with an amount of Zebularine (or an analog or a derivative thereof that retains hypomethylating activity) effective to inhibit the DNA methyltransferase. Such methods can be carried out in vivo or in vitro; in particular embodiments in which the method is carried out within a cell, the cell may be a bacterial cell, a protist cell, a fungal cell, a plant cell, or an animal cell, for instance. It is particularly contemplated that, in some cases, the cell is known to comprise or suspected of comprising a hypermethylated nucleic acid molecule (e.g., one that includes at least one CpG dinucleotide).

Another embodiment provides methods of reducing, preventing or reversing DNA methylation in a cell, which methods involve administering a hypomethylating effective amount of Zebularine to the cell, thereby reducing, preventing or reversing DNA methylation in the cell (e.g., a bacterial cell, a protist cell, a fungal cell, a plant cell, or an animal cell). In some examples of these methods, a nucleic acid in the cell is known to be or suspected of being hypermethylated. In particular contemplated examples, the cell to which Zebularine is administered is a hyper-proliferative cell (e.g., a mammalian tumor cell).

A further embodiment is a method of treating or ameliorating a hypermethylation-related disease, condition, or disorder in a subject, which method involves administering to the subject a hypomethylating effective amount of Zebularine, or an analog or a derivative thereof that retains hypomethylating activity (e.g., in the form of a pharmaceutical composition). In examples of this method, the disease is a hyper-proliferative disease, for instance a mammalian neoplasm.

Methods of ameliorating a tumorigenic state of a cell are also provided. In such methods, a hypomethylating effective amount of Zebularine, or an analog or a derivative thereof, such as a compound bearing a 2-pyrimidinone moiety, that retains hypomethylating activity (e.g., in the form of a pharmaceutical composition) is administered to the cell to reduce methylation of cytosine in a CpG dinucleotide in the cell, thereby ameliorating the tumorigenic state of the cell. In examples of these methods, one or more anti-cancer agents are also administered to the cell. In particular embodiments, the cell to which Zebularine is administered is a cell in a subject, such as a tumor cell.

In some examples of the provided method, the active compound (e.g., Zebularine) is incorporated into an oligonucleotide.

Also provided are methods of inhibiting methylation of a target sequence (e.g., one which includes at least one CpG dinucleotide), which methods involve contacting the sequence with a derivatized oligonucleotide complementary to at least a portion of the target sequence. In these methods, the derivatized oligonucleotide includes at least one Zebularine residue or hypomethylating effective derivative thereof. Specific examples of target sequences include regulatory regions of tumor suppressor genes, including those tumor suppressor genes known to be or suspected of being inactivated by methylation. Examples of these methods of inhibiting methylation occur inside of a cell, for instance a bacterial cell, a protist cell, a fungal cell, a plant cell, or an animal cell.

Another embodiment is a derivatized oligonucleotide that includes at least one Zebularine residue, or at least one hypomethylating effective derivative of Zebularine. Examples of such oligonucleotides have a sequence that is homologous to a sequence within a tumor suppressor gene regulatory region.

Also provided are derivatives of Zebularine, wherein the derivative is substantially stable in a biological system and retains hypomethylating activity compared to Zebularine. In some specific examples, such derivatives have greater hypomethylating activity compared to Zebularine.

Further embodiments include kits for inhibiting a DNA methyltransferase, which kits include an amount of Zebularine (e.g., in the form of a pharmaceutical composition) effective to inhibit the DNA methyltransferase and optionally may include instructions for using the kit for its intended purpose(s). Specific examples of such kits are useful for treating hyper-methylation mediated disease or disorder in a subject suspected of needing such inhibition, for instance a subject known to or suspected of suffering from a methylation-linked disease or disorder.

IV. Zebularine as an Inhibitor of DNA Methylation

Zebularine (FIG. 1), also known as 1-β-ribofuranosyl-1,2-dihydropyrimidin-2-one and 1-β-ribofuranosyl-2(1H)-pyrimidinone, has been attributed with cytidine deaminase inhibiting activity (see, e.g., Kim et al., *J. Med. Chem.* 29:1374-1380, 1986; WO 00/51639, issued to Greer, and entitled "Dramatic Simplification of a Method to Treat Neoplastic Disease by Radiation;" McCormack et al., *Biochem Pharmacol.* 29:830-832, 1980).

Zebularine and 5-fluoro-zebularine have been shown to bind at the active site of cytidine deaminase as covalent hydrates (Betts et al., *J. Mol. Biol* 235:635-656, 1994; Xiang et al., *Biochemistry* 34:4516-4523, 1995; and Frick et al., *Biochemistry* 28:9423-9430, 1989). These compounds have been proposed as candidates for use in combination chemotherapy with ara-C or 5-aza-cytidine (McCormack et al., *Biochem. Pharmacol.* 28:830-832, 1980; and Laliberte et al., *Cancer Chemother. Pharmnacol.* 30:7-11, 1992). In addition, it was reported that Zebularine had antitumor activity (Driscoll et al., *J. Med. Chem.* 34:3280-3284, 1991) when given orally, though no mechanism has previously been determined for this activity.

It has been surprisingly found that Zebularine is a potent, low toxicity inhibitor of DNA methylation (a hypomethylating agent). As described more fully below, Zebularine shows hypomethylating activity in the *N. crassa* in vivo system for measuring methylation (Example 1), and in mammalian cell lines such as the human bladder carcinoma cell lines T24 and normal mouse embryonic fibroblast cell line 10T1/2 (Examples 2 and 3).

Figure 1:
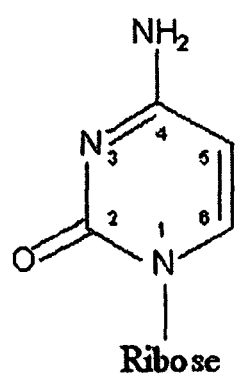
FIG. 1 shows the chemical structure of cytidine, and the cytidine analogs 5-azacytidine and Zebularine.
Figure 1:
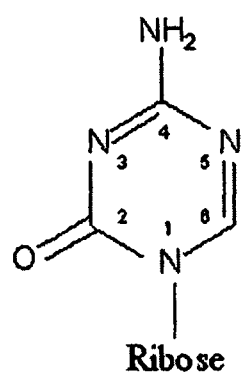
Figure 1:
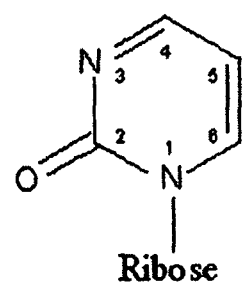

The compounds 5-azacytidine (5-Aza-CR; FIG. 1) and 5-Aza-2'-deoxycytidine (5-Aza-CdR) have been used to inhibit DNA methylation. 5-Aza-CR and 5-Aza-CdR are metabolized (see FIG. 2) and are ultimately incorporated into cellular DNA. DNA that contains 5-Aza-CdR directly inhibits DNA methyltransferases and thus DNA methylation.

Figure 3:
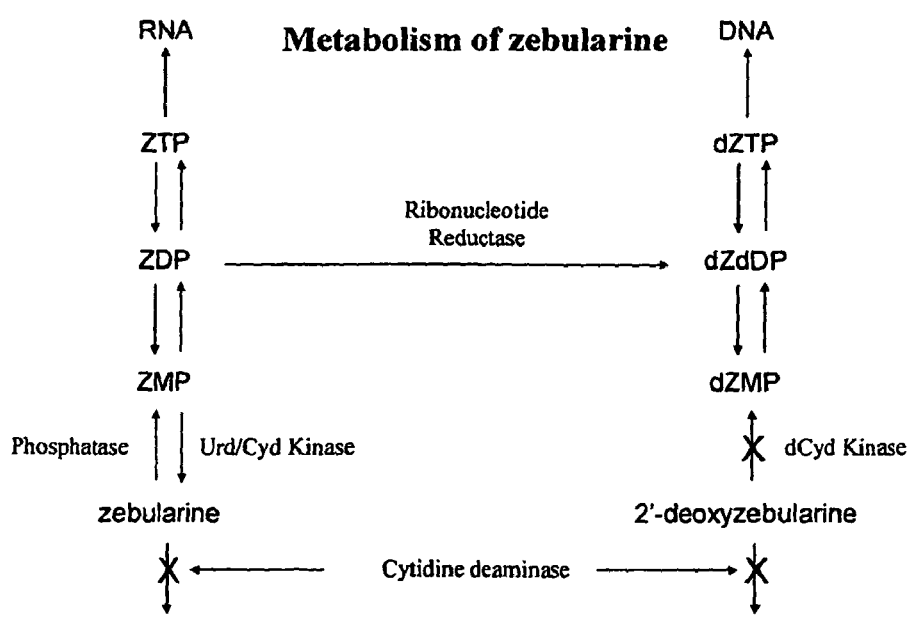
FIG. 3 is a schematic representation of the proposed metabolism of Zebularine and 2'deoxy-Zebularine.

Zebularine is a modified pyrimidine ribonucleoside that can be incorporated into RNA or, following conversion to the corresponding 2'-deoxy compound, into DNA (Jeong et al., *J. Med. Chem.* 41:2572-2578, 1998; Betts et al., *J. Mol. Biol.* 235:635-656, 1994; Xiang et al., *Biochem.* 34:830-832, 1995; and Frick et al., *Biochem.* 28:8423-9430, 1989) via a metabolic pathway that is believed to be identical or similar to that schematically represented in FIG. 3.

While not wishing to base the method or the practice of it on any particular theory or set of theories, the inventors recognize that Zebularine's ability to inhibit DNA methylation may be caused by incorporation into DNA of Zebularine's 2-pyrimidinone ring as an alternative base. Alternatively, Zebularine's hypomethylating activity may arise when it is incorporated into RNA. Further, the inventors recognize in vivo effects observed for Zebularine may arise from direct inhibition of a DNA methyltransferase, or via an indirect mechanism, such as interference with RNA silencing mechanisms (see, e.g., Plasterk, *Science,* 296:1263-1265, 2002).

Zebularine is a substrate for uridine kinase (UK) and human tumor cells exhibit elevated UK activity. This raises the possibility that Zebularine may operate through a biologically active, phosphorylated derivative via a mechanism selective for tumor cells. See, Weber, et al., *Cancer Biochem. Biophys.* 16:1-15, 1998.

The inventors further recognize that DNA methylation may be inhibited by delivery into an organism of one or more "prodrugs." Such prodrugs may include, for example and without limitation, the mono-, di-, or tri-phosphate derivatives of zebularine or its analogs and homologs; the mono-, di-, or tri-phosphate derivatives of 2'-deoxyzebularine or its analogs or homologs; or any other compounds that result in the delivery of an effective amount of 2-pyrimidinone or a derivative thereof to cells, particularly those that result in the incorporation of a 2-pyrimidinone moiety into DNA and/or RNA as an alternative base. Various forms of prodrugs are well known in the art. For examples of such prodrugs derivatives, see, e.g., *Methods in Enzymology,* 42:309-396, 1985, which is incorporated herein by reference. Particular contemplated prodrugs include "masked" phosphates of Zebularine and 2'-deoxy Zebularine, including masked monophosphates of 2'-deoxy Zebularine, and particularly including phosphoesters, phosphoethers, and alkylated derivatives.

It is understood that certain of the compounds described above may form salts with alkali metals, such as sodium, potassium and lithium, with alkali earth metals, such as calcium, magnesium and barium, with organic bases, such as amine bases, for example, dicyclohexylamine, pyridine, arginine, lysine and the like. Other compounds, such as the prodrugs described above, may form salts with a variety of organic and inorganic acids. Solely by way of example, such salts may include those formed with hydrogen chloride, hydrogen bromide, methanesulfonic acid, toluene sulfonic acid, citric acid, tararic acid succinic acid, acetic acid, trifluoroacetic acid, and various others of the like.

Interestingly, the first enzyme believed to be involved in activating Zebularine (uridine-cytidine kinase) is elevated above normal levels in many human tumors, including human ovarian, breast, rectal, and lung tumors (see Example 4). Because this enzyme may be important in the in vivo hypomethylating activity of Zebularine, its elevation in tumor tissue provides a mechanism for preferential activity of the drug in those tissues most in need of reduction of (or reversal of) DNA methylation.

Zebularine exhibits some toxicity in both *Neurospora* and mammalian cells (see, Example 2 and FIG. 6). This toxicity is substantially lower than that observed with 5-Aza-CR, and appears not to be mediated by its inhibition of DNA methyltransferase (Example 1).

Table 1 provides a summary of chemical and biological characteristics of Zebularine in comparison to the known DNA methyltransferase inhibitor 5-azacytidine.

TABLE 1

Summary of characteristics of 5-Azacytidine and Zebularine

| Properties | 5-aza-CR | Zebularine |
|---|---|---|
| Chemical Formula | $C_8H_{12}N_4O_5$ | $C_9H_{12}N_2O_5$ |
| Molecular Weight | 244.2 g/mol | 228.2 g/mol |
| Stability | Unstable at neutral pH in aqueous solution | Decomposes only at high pH values (pH > 12) |

TABLE 1-continued

Summary of characteristics of 5-Azacytidine and Zebularine

| Properties | 5-aza-CR | Zebularine |
|---|---|---|
| Half-life | 90 min.* | N/A |
| Toxicity | High | Low |
| $UV_{max}$ | 241 nm ($\epsilon$ = 8767) | 330 nm |
| Role of Action | DNA Methylation Inhibitor | DNA Methylation Inhibitor and Cytidine Deaminase Inhibitor |

*Illustrated half-life is at 50° C. in PBS, pH 7.4; the half-life of 5-Aza-CR is dependent on solution conditions (e.g., pH, temperature, and so forth); see, for instance, Chan et al., J. Pharma. Sci. 68: 807-812, 1979; Chatterji and Gallelli, J. Pharma. Sci. 68: 822-826, 1979).

V. Use of Zebularine to Treat, Cure, Ameliorate, or Prevent a Hypermethylation-Linked Disease, Disorder or Condition With the identification of the hypomethylation activity of Zebularine, the benefits of using this compound to ameliorate, prevent, or treat diseases and conditions that involve hypermethylation is now enabled.

Hypermethylation-associated diseases, disorders, and conditions are characterized by exhibiting hypermethylation of one or more DNA sequences. Such diseases, disorders, and conditions therefore can be identified by examining the methylation state (or level) of nucleic acids in a subject known to or suspected of suffering therefrom; a high level of specific or general DNA methylation indicates that the diseasel/disorder/condition is hypermethylation-associated. It is beneficial to treat (or prevent) such diseases, disorders, and conditions with Zebularine, for instance a Zebularine-comprising composition such as a pharmaceutical composition.

In certain embodiments therefore, prior to administration of Zebularine, subjects will be screened to find those whose condition involves hypermethylation of one or more DNA sequences, and thus are most likely to be susceptible to treatment with Zebularine. Such screening in some embodiments involves examining the methylation level of the genome of cell or tissue sample from the subject, or of a specific target sequence from such genome. In some embodiments, screening involves detecting the level of uridine-cytidine kinase in a cell or tissue. In particular embodiments, both the methylation state and level of uridine-cytidine kinase are tested prior to selecting Zebularine (or a derivative thereof) for use in a treatment. Methods for testing both uridine-cytidine kinase levels and methylation state are provIded herein.

Zebularine's activity as a hypomethylation agent is thought to be effective in any system that is subject to DNA methylation. Thus, though several of the illustrated examples are based on animal disease systems, such as hyper-proliferative disorders including tumors, it is also contemplated that Zebularine is useful in other systems. For instance, Zebularine presumably can be used to alter the methylation state of DNA in plants, including transformed plants that have undergone methylation-mediated gene silencing or silenced plant developmental genes (see for instance, U.S. Pat. No. 6,011,200, entitled "Methods for Altering the Rate of Plant Development and Plants Obtained Therefrom").

Other processes are mediated by methylation of DNA, and Zebularine presumably can be used to influence these processes by altering the DNA methylation state of the system. In particular, it is contemplated that the hypomethylation activity of Zebularine can be used to reduce antimicrobial resistance, similarly to the system described in U.S. Pat. No. 5,872,104 (entitled "Combinations and Methods for Reducing Antimicrobial Resistance"). Examples of such methods work by reducing the methylation-mediated binding inhibition of an antibiotic agent, for instance on an rRNA molecule, thereby increasing the susceptibility of the treated microbes to that antibiotic agent.

VI. Production of Zebularine and Derivatives Thereof

Methods are known for the chemical synthesis of Zebularine from commercially available intermediates. See, particularly, Liu et al., J. Med. Chem., 24:662-666, 1981, and Driscoll et al., J. Med. Chem. 34:3280-3284, 1991. Analogs have been previously synthesized, for instance as described in Kim et al., J. Med. Chem. 29:1374-1380, 1986. The synthesis of nucleotides containing zebularine has been described, for instance, in Barchi et al. (J. Enzyme Inhib. 9:147-162, 1995).

Also encompassed herein are methods that use a prodrug of 2'-deoxyzebularine, for instance such as can be made using the methodology described by Meier et al. (ChemBioChem, 2:283-285, 2001). It is believed that using a pro-drug bypasses the first kinase step in in vivo processing of the compound; this kinase is believed not to be active with 2'-deoxyzebularine (see FIG. 3).

Derivatives of Zebularine can be produced using well known chemical methods, for instance by substitution or addition of one or more side groups on Zebularine for other organic groups, halogens, and so forth. Some derivatives have been published previously (Barchi et al., J. Enzyme Inhib. 9:147-162, 1995; Driscoll et al., J. Med. Chem. 34:3280-3284, 1991). Particular contemplated analogs and derivatives of Zebularine include variations of the pyrimidinone group and/or the ribose moiety, such as 2'-deoxy-Zebularine, 5-fluoro-analogs of Zebularine and of 2'-deoxy-Zebularine, and 4,6-difluoro analogs of Zebularine and 2'-deoxy-Zebularine. Additional contemplated analogs and derivatives of Zebularine include variations on the carbohydrate moiety, such as halogenated derivatives, for example 2'-deoxy-2'-fluoro-ribose derivatives. Particular derivatives, including prodrugs of Zebularine are represented by the structure of Formula 1.

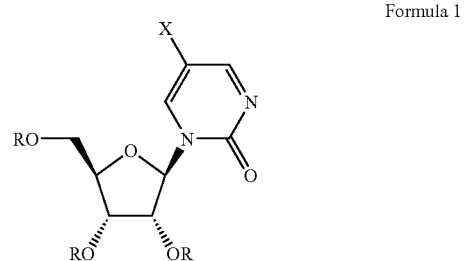

Formula 1

With reference to Formula 1, R groups independently are H or groups cleaved during metabolism of the compound to release Zebularine or a Zebularine derivative. Thus, particular R groups independently are selected from the group consisting of carboxylic acid esters, phosphoesters and ethers. An exemplary ester R group is pivaloyl, and exemplary ethers include those where R is an alkyl group. X may be selected from the group consisting of H, F, Cl, Br, alkyl, alkenyl, and alkynyl groups. In particular examples, X may be a group according to Formula 2a or 2b. With reference to Formulas 2a and 2b, Y may be selected from the group consisting of H, carboxylic acids, carboxylic acid esters, and the halogens. Where X is a halogen, the compound may be prepared according to the method of McCormack et al., Biochem Pharmnacol. 29:830-832, 1980.

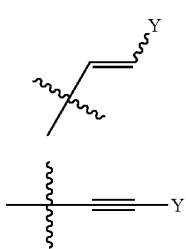

Formula 2a

Formula 2b

VII. Production of Zebularine-Derivatized Oligonucleotides and their Use

With the discovery that Zebularine is an effective hypomethylating agent, it is believed that Zebularine can,be integrated into oligonucleotides and the resultant derivatized oligonucleotides used to inhibit methylation at specific targeted sites in nucleic acid molecules.

Synthesis of Derivatized Oligonucleotides

In vitro methods for the synthesis of oligonucleotides are well known to those of ordinary skill in the art; such conventional methods can be used to produce oligonucleotides for the disclosed methods. The most common method for in vitro oligonucleotide synthesis is the phosphoramidite method, formulated by Letsinger and further developed by Caruthers (Caruthers et al., *Chemical synthesis of deoxyoligonucleotides*, in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach*, IRL Press, 1984.

In general, the synthesis reactions proceed as follows: First, a dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleoside to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for instances, U.S. Pat. Nos. 4,415,732, 4,458,066, 4,500,707, 4,973,679, and 5,132,418. Oligonucleotide synthesizers that employ this or similar methods are available commercially (e.g., the PolyPlex oligonucleotide synthesizer from Gene Machines, San Carlos, Calif.). In addition, many companies will perform such synthesis (e.g., Sigma-Genosys, TX; Operon Technologies, CA; Integrated DNA Technologies, IA; and TriLink BioTechnologies, CA).

Derivatized or modified nucleotides and nucleotide analogs, such as Zebularine and deoxy-Zebularine, can be incorporated into an oligonucleotide essentially as described above for non-modified nucleotides, once the phosphoramidite form of the nucleotide analog is produced. Phosphoramidites of nucleotides and nucleotide analogs, such as Zebularine and deoxy-Zebularine, can be synthesized and purified as described in Marasco et al., *J. Org. Chem* 57:6363-6365, 1992; see also Hurd et al., *J. Mol. Biol.* 286, 389-401, 1998. In particular, methods for producing Zebularine-containing oligonucleotides are conventional. The standard oligonucleotide synthesis methodology can be modified to deal with the instability of the 2-pyrimidinone ring during synthesis; see Zhou et al., *Nucleic Acids Res.* 24,:2652-2659, 1996; Adams et al. *Tetrahedron Lett.* 35:1597-1600, 1994; and Gildea et al., *Nucleic Acids Res.* 17:2261-2281, 1989.

Uses of Derivatized Oligonucleotides

Oligonuclcotides that have been derivatized to contain at least one zebularine residue (or an analog thereof that maintains hypomethylating activity) can be used to inhibit methylation at a target nucleic acid sequence substantially homologous to the oligonucleotide. This disclosure specifically contemplates methods of inhibiting methylation of a target sequence, which methods involve contacting a cell containing that sequence with a Zebularine-derivatized oligonucleotide complementary to at least a portion of the target sequence. In specific embodiments, the target sequence contains one or more CpG dinucleotides. Specific examples of target sequences include regulatory regions of genes, such as tumor suppressor genes.

Zebularine-derivatized oligonucleotides also can be used to elucidate the mechanism(s) of Zebularine's hypomethylating activity. By comparing the inhibitory potency of an oligonucleotides containing 2'-deoxy-zebularine with similar sequences containing other inhibitors (e.g., 5-fluoro-2'-deoxycytidine or 5-aza-2'-deoxycytidine), it will be possible to determine whether Zebularine is a weaker inhibitor of methylation due to low incorporation into DNA, or another inherent low inhibiting activity.

Zebularine-derivatized oligonucleotides also can be used to elucidate the mechanism(s) of Zebularine's hypomethylating activity. By comparing the inhibitory potency of an oligonucleotides containing 2'-deoxy-Zebularine with similar sequences containing other inhibitors (e.g., 5-fluoro-2'-deoxycytidine or 5-aza-2'-deoxycytidine), it will be possible to determine whether Zebularine is a weaker inhibitor of methylation due to low incorporation into DNA, or another inherent low inhibiting activity. If the level of inhibition provided by the derivatized oligonucleotides, including Zebularine, is comparable or identical to each other, it is contemplated that Zebularine's hypomethylating activity can be enhanced by administering a Zebularine pro-drug. This enables more of the drug to be incorporated into DNA and thus the drug to be relatively more potent. Investigation of the derivatized oligonucleotides, and particularly their capacity to inhibit DNA methylation, can be performed as reported in Sheikhnejad et al. (*J. Mol. Biol.* 285,:2021-2034, 1999) and Marquez et al. (*Antisense & Nucleic Acid Drug Dev.* 9:415-421, 1999).

One specific Zebularine-derivatized oligonucleotide has the following sequence: TGTCAGXGCATGG (SEQ ID NO: 20), wherein X represents 2'-deoxy-Zebularine. This oligonucleotide is directed to the HhaI methylase, as described in Wang et al. (*J. Am. Chem. Soc.* 122:12422-12434, 2000). As indicated in Sheikhnejad et al. (*J. Mol. Biol.* 285:2021-2034, 1999) and Marquez et al. (*Antisense & Nucleic Acid Drug Dev.* 9:415-421, 1999), other sequences to target mammalian enzymes can be synthesized. With reference to FIG. 20, this oligonucleotide was synthesized and compared to an oligonucleotide of the same sequence having 2'-deoxy-5-azacytidine in place of the 2'-deoxy-Zebularine. Both modified oligodeoxynucleotides, as annealed duplexes with the complementary strand having 5-methylcytidine for pairing with 2'-deoxy-Zebularine and 2'-deoxy-5-azacytidine, inhibited methylation of the substrate oligonucleotide to the same extent.

VIII. Detecting/Measuring DNA Methylation

One class of methods used for determining and/or measuring the 5-methyl state of a cytosine in a nucleotide relies on using methylation-sensitive restriction endonucleases (RE). Each RE can "cut" DNA at a certain short (e.g., 4-8 nucleotide) recognition sequence. The position of such cuts can be determined based on the length of fragments produced after a digestion reaction, which fragments are detected, for instance, by gel electrophoresis, transfer to a membrane and hybridization. Certain REs are "methylation-sensitive" in that certain bases within the recognition sequence must be unmethylated at particular adenine and/or cytosine residues for digestion to occur. Indeed, certain REs, termed isoschizomers, recognize the same sequences, but are either methyl sensitive or insensitive. Examples of methylation-sensitive REs include Sau3AI and DpnII. The band pattern after digestion with a methylation-sensitive RE changes depending on the methylation pattern of the DNA. Techniques based on methylation-sensitive REs can be somewhat limited, because many CpG's that might be methylated are outside the recognition sequences of REs, and thus cannot be examined using these methods.

Methods also are available to examine individual potential methylation sites. See, for instance, Shemer et al. (*PNAS* 93:6371-6376, 1996) and Kafri et al. (*Genes Dev.* 6:705-714, 1992), which describe a PCR-based method to detect methylation in a specific target sequence.

Other methods for determining/measuring the presence of 5-methylcytosine are based on specific reaction of bisulfite with cytosine. When cytosine is reacted with bisulfite it forms uracil; 5-methylcytosine is not modified. This makes cytosine and 5-methylcytosine chemically distinguishable, due to base pairing of the reacted cytosine (now uracil) with adenine in nucleic acid hybridization reactions. For examples of such methods, see, Frommer et al., *Proc. Natl. Acad. Sci. USA* 89:1827-1831, 1992; Sadri and Hornsby, *Nuc. Acids Res.* 24:5058-5059, 1996; Warnecke et al., *Nuc. Acids Res.* 25:4422-4426, 1997; Ziong and Laird, *Nuc. Acids Res.* 25:2532-2534, 1997; Selker et al., *Science* 262:1724-1728, 1993; and Gonzalgo and Jones, *Nuc. Acids Res.* 25:2529-2531, 1997.

Another method for quantitation of methylation is the Methylation-sensitive Single Nucleotide Primer Extension (Ms-SNuPE) assay, described in Gonzalgo and Jones (*Nucleic Acids Res.* 25:2529-2531, 1997) and U.S. Pat. No. 6,251,594. This procedure provides a quantitative measurement of methylation levels of specific CpG sites in DNA. Briefly, genomic DNA is treated with bisulfite as discussed above. The DNA region of interest is then amplified by PCR, and primers are annealed to the PCR product and terminated immediately 5' to the original CpG site of interest. Quantitation of the relative ratios of methylated vs. unmethylated cytosines (C or T) is determined by incubating the annealed product with Taq polymerase and either $(a-^{32}P)$ dCTP or $(a-^{32}P)$ dTTP, followed by gel electrophoresis and PhosphorImager analysis.

High-throughput methylation assays are also useful for measuring methylation. For instance, one such assay is the Methylight assay (Eads et al., *Cancer Res.* 61:3410-3418, 2001; published international patent application PCT/US00/13029), a high-throughput quantitative methylation assay that utilizes fluorescence-based real-time PCR (TaqMan) technology.

The patent literature is also replete with methods for detecting and/or measuring methylation in a nucleic acid molecule. See, for instance:

U.S. Pat. No. 5,786,146 (entitled "Method of detection of methylated nucleic acid using agents which modify unmethylated cytosine and distinguishing modified methylated and non-methylated nucleic acids");

U.S. Pat. No. 5,871,917 (entitled "Identification of differentially methylated and mutated nucleic acids");

U.S. Pat. No. 6,017,704 (entitled "Method of detection of methylated nucleic acid using agents which modify unmethylated cytosine and distinguishing modified methylated and non-methylated nucleic acids");

U.S. Pat. No. 6,200,756 (entitled "Methods for identifying methylation patterns in a CpG containing nucleic acid");

U.S. Pat. No. 6,214,556 (entitled "Method for producing complex DNA methylation fingerprints"); and U.S. Pat. No. 6,251,594 (entitled "Cancer diagnostic method based upon DNA methylation differences").

Specific examples of methylation quantitation and detection methods are illustrated in the Examples, below.

IX. Methods of Treatment

The present disclosure includes a treatment for methylation-mediated disease such as a hyper-proliferative disease or disorder, in a subject. The method includes administering the compound Zebularine, or an analog, mimetic, or derivative thereof that has similar hypomethylation function, or a combination of such compound and one or more other pharmaceutical agents, to the subject in a pharmaceutically compatible carrier and in an amount effective to inhibit the development or progression of a methylation-mediated disease. Although the treatment can be used prophylactically in any patient in a demographic group at significant risk for such diseases, subjects can also be selected using more specific criteria, such as a definitive diagnosis of the disease/condition or identification of one or more factors that increase the likelihood of developing such disease (e.g., a genetic, environmental, or lifestyle factor).

The vehicle in which the drug is delivered can include pharmaceutically acceptable compositions of the compounds, using methods well known to those with skill in the art. Any of the common carriers, such as sterile saline or glucose solution, can be utilized. Routes of administration include but are not limited to oral and parenteral routes, such as intrathecal, intravenous (iv), intraperitoneal (ip), rectal, topical, ophthalmic, nasal, and transdermal.

The compounds may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in Remington: *The Science and Practice of Pharmacy* (19th Edition, 1995) in chapter 95.

Embodiments of other pharmaceutical compositions can be prepared with conventional pharmaceutically acceptable carriers, adjuvants, and counter-ions as would be known to those of skill in the art. The compositions in some embodiments are in the form of a unit dose in solid, semi-solid and liquid dosage forms such as tablets, pills, powders, liquid solutions, or suspensions.

The compounds of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated, for instance in order to reduce the occurrence of remethylation of a tumor suppressor gene.

Zebularine's role in reactivating tumor suppressor genes also makes it a good candidate for follow-up therapy after radiation or conventional chemotherapy to avoid recurrence of the tumor. In certain embodiments, Zebularine can reactivate a glycoprotein that prevents cell migration and/or a gene that encodes a hormone receptor. The tumor load cannot be too great for Zebularine to act properly.

In some embodiments, sustained intra-tumoral (or near-tumoral) release of the pharmaceutical preparation that comprises a hypomethylation effective amount of Zebularine may be beneficial. Slow-release formulations are known to those of ordinary skill in the art. By way of example, polymers such as bis(p-carboxyphenoxy)propane-sebacic-acid or lecithin suspensions may be used to provide sustained intra-tumoral release.

It is specifically contemplated in some embodiments that delivery is via an injected and/or implanted drug depot, for instance comprising multi-vesicular liposomes such as in DepoFoam (SkyePharma, Inc, San Diego, Calif.) (see, for instance, Chamberlain et al., *Arch. Neuro.* 50:261-264, 1993; Katri et at., *J. Pharm. Sci.* 87:1341-1346, 1998; Ye et al., *J. Control Release* 64:155-166, 2000; and Howell, *Cancer J.* 7:219-227, 2001).

In other embodiments, perfusion of a tumor with a pharmaceutical composition that contains a hypomethylation effective amount of Zebularine is contemplated.

Therapeutically effective doses of the compounds of the present disclosure can be determined by one of skill in the art. The low toxicity of the compound makes it possible to administer high doses, for example 100 mg/kg, although doses of 10 mg/kg, 20 mg/kg, 30 mg/kg or more are contemplated. An example of such a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 1.0 to 1000 mg of the active ingredient, particularly 1, 5, 10, 15, 20, 25, 50, 100, 200, 400, 500, 600, 800, and 1000 mg of the active ingredient for the symptomatic adjustment of the dosage to the subject being treated.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The pharmaceutical compositions comprising a hypomethylation effective amount of Zebularine can be used in the treatment or prevention of a variety of diseases and conditions that are associated with and/or caused by hypermethylation of one or more gene sequences. Examples of such diseases include cancers, in particular tumors that are characterized by having one or more hypermethylated sequences such as a tumor suppressor gene, particularly where the hypermethylation has resulted in the inactivation (silencing) of that gene. Many of such inactivated genes and associated cancers have now been identified, including for instance: cadherin (inactivation of which is often associated with breast or prostate tumors and squamous cell lung carcinoma, and the migration of tumor cells to distant nodes); estrogen receptor (inactivation of which is often associated with estrogen receptor negative breast tumors; reactivation of the receptor leads to potential by, for example, tamoxifen); VHL (inactivation of which is associated with renal cancer); H19 (a tumor suppressor gene located on 11p, the inactivation of which is implicated in many tumors); 14-3-3 σ (silenced in some breast cancers); Apaf-1 (inactivated in metastatic melanomas, though it appears that the methylation inactivation related to this gene may be indirect or through a genetic region other than the Apaf-1 promoter); and p53 (a tumor suppressor gene, the inactivation of which is implicated in many tumors, particularly unstable tumors). In addition, hypermethylation at CpG islands which are not or have not yet been associated with a specific gene, such as the one identified at 17p13.3, can contribute to cancer formation.

It is believed that several other genes show activities that help to inhibit tumor growth, aggressiveness, and/or metastasis. Methylation-mediated inactivation of any of these genes may lead to increased tumorigenesis, metastasis, and/or more highly aggressive tumors, and thus inhibition or reversal of methylation-mediated inactivation of these genes using Zebularine can be beneficial in controlling cancers. Examples of such genes include glutathione-S-transferase (GST), methyl guanine methyltransferase, and TIMP-3 (tissue inhibitor of metalloproteinase-3).

As a consequence of DNA methylation, methylcytidine can be deaminated. Methyldeoxycytidine, when deaminated, becomes thymidine, and pairs with deoxyadenosine rather than deoxyguanidine, so that a CG base pair is converted to a TA pair, leading to mutation. In addition, some cancers arise from or are enhanced by mutations in genes where the mutation is thought to have been caused by methylation of a cytidine residue, followed by the subsequent conversion of the methylated deoxycytidine to a thymidine. This often occurs with the tumor suppressor p53. Thus the methyltransferase causes mutational hot spots. This can result in tumor gene unstabilization, tumor metastasis, tumor progression, tumor recurrence and resistance of the tumor to therapy by cytotoxic agents. Subclones of the tumor containing the mutated gene(s) may be more aggressive, metastatic, and therapy resistant. It is believed that Zebularine hypomethylation activity can be used to prevent or reduce the likelihood of such mutations.

X. Combination Therapy

The present disclosure also contemplates combinations of Zebularine compounds with one or more other agents useful in the treatment of hypermethylation-related disease. For example, the compounds of this disclosure may be administered in combination with effective doses of other medicinal and pharmaceutical agents. In some embodiments, one or more known anti-cancer drugs are included with the Zebularine. The term "administration in combination with" refers to both concurrent and sequential administration of the active agents.

In addition, the compounds and/or peptides of this disclosure may be administered in combination with effective doses of radiation, anti-proliferative agents, anti-cancer agents, immunomodulators, anti-inflammatories, anti-infectives, hypomethylation agents, nucleosides and analogs thereof, and/or vaccines.

Examples of anti-proliferative agents that can be used in combination with Zebularine include, but are not limited to, the following: ifosamide, cisplatin, methotrexate, procarizine, etoposide, bischloroethyl nitrosourea (BCNU), vincristine, vinblastine, cyclophosphamide, gemcitabine, 5-fluorouracil, paclitaxel, or doxorubicin.

Non-limiting examples of immuno-modulators that can be used in combination with Zebularine are AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Specific examples of compounds that in some embodiments are used in combination with Zebularine are 5-azacytidine, tetrahydrouridine, 2'-deoxy-4-azacytidine, ara-C, and tricostatin A. It is believed that such agents may be additive and/or synergistic with Zebularine in inhibiting DNA methylation. An exemplary synergistic effect is derived by coadministration or pre-administration of tetrahydrouridine or other inhibitors of cytidine deaminase, so that the amount of Zebularine bound by the enzyme is reduced. Zebularine is thus free to be further processed, for example, incorporated into a nucleic acid; or Zebularine can bind to another enzyme or receptor, thereby acting, for example, as a hypomethylating agent. In other words, a cytidine deaminase inhibitor, such as tetrahydrouridine, can function to block this enzyme from binding Zebularine, thereby increasing the effective Zebularine concentration. Tetrahydrouridine has been shown to be safe and non toxic in mammalian cells. See, Cooper and Greer, "The Effect of Inhibition of Cytidine Deaminase by Tetrahydrouridine on the Utilization of Deoxycytidine and 5-bromodeoxycytidine for DNA Synthesis", *Mol. Pharm.* 9:698-703 (1973). See also, Wong et al., *Proc. Am. Assoc. Cancer Res. and ASCO,* 1977.

The combination therapies are of course not limited to the lists provided in these examples, but includes any composition for the treatment of diseases or conditions associated with hypermethylation of one or more gene sequences.

XI. Kits

The Zebularine and related compounds disclosed herein can be supplied in the form of kits for use in inhibiting a DNA methyltransferase, kits for use in reducing the methylation of a nucleic acid, and kits for prevention and/or treatment of a disorder, condition or diseases (e.g., a hyper-proliferative disorder, such as neoplasm, in particular a hyper-proliferative disorder that is mediated by methylation of one or more gene sequences). In such a kit, a hypomethylating effective amount of one or more of the compounds is provided in one or more containers. The compounds may be provided suspended in an aqueous solution or as a freeze-dried or lyophilized powder, for instance. In certain embodiments, the compounds will be provided in the form of a pharmaceutical composition.

Kits can also include instructions, usually written instructions, to assist the user in treating or preventing a disorder, condition or disease (e.g., a methylation-mediated hyperproliferative disorder) with a kinase-activity modifying compound and/or binding peptide. Such instructions can optionally be provided on a computer readable medium.

The container(s) in which the compound(s) are supplied can be any conventional container that is capable of holding the supplied form, for instance, microfuge tubes, ampoules, or bottles. In some applications, the therapeutic compound may be provided in pre-measured single use amounts in individual, typically disposable, tubes, or other such containers.

The amount of a compound supplied in the kit can be any appropriate amount, depending for instance on the market to which the product is directed. For instance, if the kit is adapted for research or clinical use, the amount of each hypomethylating compound (e.g., Zebularine) provided likely would be an amount sufficient for several treatments.

Certain kits will also include one or more other agents useful treating or preventing a disease or condition, for instance an agent useful in inhibiting cell proliferation that is mediated by or influenced by hypermethylation of a gene sequence, e.g. in treating hyper-proliferation of a methylation-associated tumor. For example, such kits may include one or more effective doses of anti-proliferative or anti-cancer drugs.

The invention is illustrated by the following non-limiting Examples.

EXAMPLES

Example 1

Inhibition of DNA Methylation in Neurospora

This example provides methods for assessing the hypomethylation/demethylation activity of Zebularine, or related compounds, in *Neurospora crassa*, which serves as a convenient laboratory system for DNA methylation studies.

Materials and Methods

Strains and Cultures

*N. crassa* strains N644, N242 and N613, and culture conditions, were as previously described (Selker, *Proc. Natl. Acad. Sci. USA* 95:9430-9435, 1998).

Southern Blot Analysis

Figure 4A:
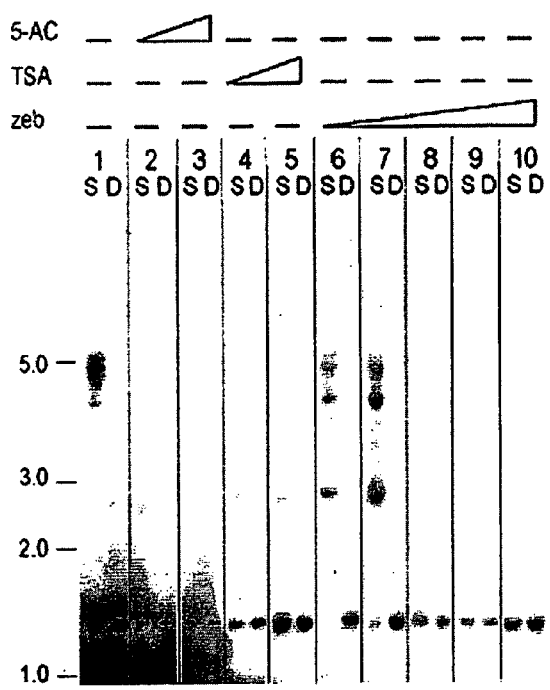
FIG. 4 shows Southern blots of DNA from *N. crassa*, showing the effects of 5-azacytidine (5-AC), trichostatin A (TSA) and Zebularine on DNA methylation of the am$^{RIP}$ and ψ63 sequences. DNA was digested with Dpn II (D) or Sau3AI (S), fractionated by gel electrophoresis, transferred to a membrane and probed for am (FIG. 4A) or ψ63 (FIG. 4B) sequences. Dpn II and Sau3AI both recognize the sequence GATC, but Sau3AI fails to cleave if the C residue is methylated. Thus, differences between S and D lanes are indicative of DNA methylation.
Figure 4B:
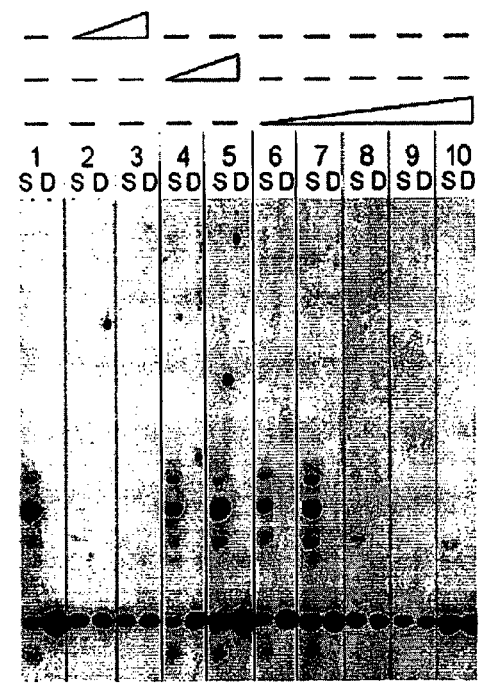

Southern hybridizations were performed on DNA samples ($-1$ µg) isolated from liquid cultures inoculated with $7 \times 10^4$ conidia/ml. DNA was digested with Dpn II (D) or Sau3AI (S), fractionated by gel electrophoresis, transferred to a nylon membrane and probed for $am^{RIP}$ (FIG. 4A) or $\psi 63$ (FIG. 4B) sequences. The restriction endonucleases Dpn II and-Sau3AI both recognize the sequence GATC, but Sau3AI fails to cleave if the C residue is methylated. Drug concentrations were 12 and 24 mM 5-AC, 0.33 and 3.3 µM TSA, and 0.19, 0.39, 0.78, 1.6 and 3.1 µM Zebularine.

Plate Assays

Plate tests were performed with solidified medium essentially as previously described (Selker, *Proc. Natl. Acad. Sci. USA* 95;9430-9435, 1998). In brief, approximately 2,000 *N. crassa* conidia of the indicated were plated on each plate. Drugs were administered from a 4-mm diameter Whatman™ no. 1 paper disk placed in the middle of each plate shortly after plating.

Results

Treatment with Zebularine Reduced Methylation in *N. crassa*.

The results of a representative experiment are shown in FIG. 4. The positions of selected size standards (kb) and the origin (ori) are indicated. A control hybridization (not shown in the figure) indicated that the digests were complete. Differences between S and D lanes are indicative of DNA methylation.

These data indicate that Zebularine inhibits DNA methylation globally, like 5-AC, as opposed to the selective inhibition of methylation caused by TSA, a known inhibitor of histone deacetylase (Selker and Stevens, *Proc. Natl. Acad Sci. USA* 82, 8114-8118, 1985; Selker, *Proc. Natl. Acad. Sci. USA*

95, 9430-9435, 1998). It is believed that the hypomethylating activity of Zebularine occurs by a mechanism similar to 5-azacytidine.

Reactivation of Silenced hph Gene by Zebularine.

*N. crassa* was used to quantitatively examine the effectiveness of Zebularine at reducing or reversing methylation (Selker, *Proc. Natl. Acad. Sci. USA*, 95:9430-9435, 1998). *N. crassa* strain N644 has a single copy of the *Escherichia coli* hph gene that was silenced (repressed) by cytosine methylation resulting from the action of RIP on flanking direct repeats of the am gene (see Irelan and Selker, *Genetics* 146:509-523, 1997). The active hph gene confers hygromycin (hyg) resistance. Thus, growth of colonies on the plates that contain hygromycin indicates reactivation of the hph gene through loss of methylation.

Plates (FIG. 5) were treated with Zebularine (0, 2.5, 5.0, 10, 20, 100, 200, and 400 nmoles, as indicated), 20 nmoles 5-azacytidine (a known global demethylating drug used as a positive control for the RIP system), or no hygromycin (a positive control to show maximal conidia growth).

As shown by the conidia growth on plates treated with Zebularine, this compound is effective to reduce or reduce methylation, and thereby reactivate the hph gene.

Zebularine Toxicity is Not Dependent on the dim-2 DNA Methyltransferase.

Strains with mutations in dim-2 lack all detectable methyltransferase activity (Kouzminova and Selker, "Dim-2 encodes a DNA-methyltransferase responsible for all known cytosine methylation in *Neurospora*," *EMBO J.* Aug. 1, 2001). In order to examine whether Zebularine toxicity is mediated by its methyltransferase-inhibitory activity, dim-2 strain (N613) and a wild-type control (N242) were challenged with a high concentration (400 nmoles) of Zebularine. No hygromycin was applied to these plates.

FIG. 6 is a series of photographs of plate from a representative experiment, illustrating that the inhibitory growth effects of Zebularine do not depend on the dim-2 DNA methyltransferase. This is evident because the region of conidia toxicity around the Whatman™ filter disks is roughly equivalent in both dim-2 and wildtype strains treated with 400 nmoles of Zebularine.

Example 2

Inhibition of DNA Methylation in Mammalian Cells

This example provides methods that have been used to analyze the effectiveness of Zebularine for inhibiting DNA methylation in mammalian cells.

Materials and Methods

Cell Lines

Stock cultures of 10T1/2 cells between passages 7 and 15 were grown in 75 cm$^2$ plastic flasks (Falcon) in Eagle's basal medium supplemented with 10% heat-inactivated fetal calf serum and 100 U/ml penicillin-streptomycin (Gibco/Life Technologies, Inc., Palo Alto, Calif.). Cultures were grown in a humidified incubator at 37° C. in an atmosphere of 5% $CO_2$ in air.

The T24 cell line was obtained from the American Type Culture Collection (Rockville, Md.) and cultured in DMEM supplemented with 10% heat-inactivated fetal calf serum and 100 U/ml penicillin-streptomycin. Cultures were grown in a humidified incubator at 37° C. in an atmosphere of 5% $CO_2$ in air.

5-Aza-CdR, 5-Aza-CR and Zebularine Treatments

Cells were plated (3×10$^5$ cells/100-mm dish) and treated 24 hours later with the indicated concentrations of compounds. The medium was either changed 24 hours or 48 hours after drug treatment.

Induction of a Myogenic Phenotype in 10T 1/2 Cells

Myotube formation was assayed in 10T1/2 cells as previously described (Constantinides et al., Nature 267:364-366, 1977).

DNA and RNA Isolation

DNA and RNA were isolated three days after treatment using the NucleoBond RNA/DNA Midi Kit (Clontech Laboratories, Inc., Palo Alto, Calif.).

RT-PCR Analysis of Reactivated Transcripts

Total RNA (~10 μg) was reverse-transcribed using the following reagents: 100 units RNAsin (Promega Corp., Madison, Wis.), 0.1 M DTT (Life Technologies, Inc.), 1000 units of MMLV-RT (Life Technologies, Inc.), 1 mM deoxynucleotide triphosphates (Boehringer Mannheim, Germany), 75 μg/ml BSA, 1× MMLV-RT buffer (Life Technologies, Inc.), and 0.025 ODU Random Hexamers (Amersham-Pharmacia Biotech, Piscataway, N.J.). The reaction mixture was incubated for 10 minutes at 25° C., 45 minutes at 42° C., 3 minutes at 90° C., and chilled for 5 minutes at 4° C., during which time 1.25 μl of MMLV-RT (200 U/μl) were added and the sample then incubated for 45 minutes at 42° C., 10 minutes at 75° C., and stored at −20° C.

cDNA was amplified with primers specific for either p16 or GAPDH. Briefly, PCR reactions were performed in 25-μl volumes at 94° C. for 3 minutes, 28 cycles at 94° C. for 1 minute, 56° C. for 30 seconds, 72° C. for 40 seconds, and a final extension step at 72° C. for 5 min (p16 amplification), and 94° C. for 1 minute, 19 cycles at 94° C. for 1 minute, 58° C. for 30 seconds, 72° C. for 45 seconds, and a final extension step at 72° C. for 2 minutes (GAPDH amplification).

Primers sequences were as follows:

```
                                          (SEQ ID NO: 1)
p16 sense,
5'-AGC CTT CGG CTG ACT GGC TGG-3';

(SEQ ID NO: 2)
p16 antisense,
5'-CTG CCC ATC ATC ATG ACC TGG A-3';

(SEQ ID NO: 3)
GAPDH sense,
5'-CAG CCG AGC CAC ATC GCT GAG ACA-3';
and (SEQ ID NO: 4)
GAPDH antisense,
5'-TGA GGC TGT TGT CAT ACT TCT C-3'.
```

PCR amplifications were performed with cDNA template concentration equivalent to 100 ng of RNA in 10% DMSO. All reactions were analyzed in the linear range of amplification. PCR products were resolved on 2% agarose gels and subsequently transferred to a nylon membrane (Zetaprobe; Bio-Rad, Richmond, Calif.) under alkaline conditions. All blots were hybridized with a γ-$^{32}$P-labeled internal oligonucleotide probe, using protocols previously described (Xiong and Laird, *Nuc. Acids Res.* 25:2532-2534, 1997).

Results

Induction of a Myogenic Phenotype in 10T 1/2 Cells

Cytidine analogs with modifications in the five (5) position of the ring (e.g., 5-Aza-CR and 5-Aza-CdR) are powerful inhibitors of DNA methylation that can induce the formation of striated muscles cells in the non-myogenic C3H 10T1/2 C18 line of embryonic cells (Jones and Taylor, *Cell* 20:85-93, 1980). The ability of Zebularine to cause 10T1/2 cells to undergo the myogenic switch was therefore tested (FIG. 7).

Figure 2:
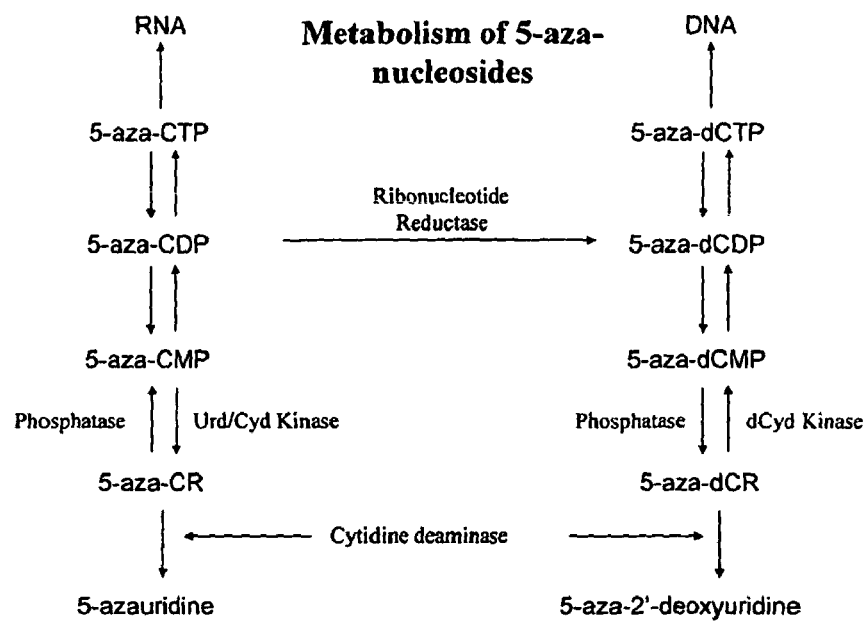
FIG. 2 is a schematic representation of the metabolism of 5-azacytidine and 5-aza-2'deoxycytidine.

Untreated 10T1/2 cells formed flat even monolayers and appeared epithelioid (FIG. 7A), while 10T1/2 cells treated with either 5-Aza-CdR (FIG. 7B) or 5-Aza-CR (FIG. 7C) formed multinucleated myotubes with regular striations approximately 9-10 days after drug treatment. Both 5-Aza-CdR and 5-Aza-CR were able to induce a tremendous number of muscle formations in 10T 1/2 cells (Table 2). Zebularine also induced muscle formation in 10T1/2 cells as shown in FIG. 2, however, the extent of muscle formation was not as great as that of either 5-Aza-CdR or 5-Aza-CR (Table 2). Since the muscle phenotype has been reported to be induced only by inhibitors of cytosine methylation, this result indicated that Zebularine inhibited DNA methylation in 10T1/2 cells.

Effects of Zebularine on p16 Expression in Human Tumor Cell Line T24

The T24 bladder carcinoma-derived cell line has been shown to contain a transcriptionally silent, hypermethylated p16 gene, which can be demethylated by 5-Aza-CdR to reactivate p16 gene expression (Gonzalgo et al., *Cancer Res.* 58:1245-1252, 1998). Since 5-Aza-CdR has been shown previously to induce p16 expression in a dose-dependent manner (Bender et al., *Cancer Res.* 58:95-101, 1998), the two ribonucleoside analogs 5-Aza-CR and Zeb were examined to determine their abilities to induce p16 expression (FIG. 8). Because Zeb is stable in aqueous solution, the effect of prolonging Zeb treatment on p16 expression was tested by treating these cells with different concentrations of Zeb for either 24 hours or 48 hours. RT-PCR was then performed to determine whether p16 gene was induced by drug treatment.

In FIG. 8, both of the negative controls (no RNA and the untreated samples) show no p16 expression. On the other hand, the positive control with 3 µM 5-Aza-CdR, resulted in a robust expression of p16 (FIG. 8).

Treatment with increasing concentration of 5-Aza-CR showed induction of p16 expression in a dose-dependent manner, with no expression observed in the 3 µM dose but a significant expression observed in the 100 µM dose. Nevertheless, the highest expression level observed with treatment of 100 µM 5-Aza-CR was only one-fifth as high as the p16 expression level observed with treatment of 3 µM 5-Aza-CdR.

Zebularine was able to induce p16 expression in both a dose-dependent manner and a time-dependent manner. Treatment with 300 µM Zeb for 24 hours was insufficient to induce p16 expression. However, p16 expression was induced with either 300 µM Zebularine for 48 hours (longer treatment) or 500 µM for 24 hours (higher dosage). At each dose of Zeb, a correlation is apparent between the time of drug treatment (24 hours to 48 hours) and the expression of p16 gene. As the treatment time increases from 24 to 48 hours, the induction of p16 expression increases correspondingly. Since the reactivation of the p16 gene has only been shown with inhibitors of cytosine methylation, this result indicated that Zebularine inhibited DNA methylation in T24 cells as well.

Example 3

Inhibition of DNA Methylation with Continuous Treatment

Using methods essentially similar to those described in Example 2, the effect of continuous, long term (40 days) treatment of T24 cells with low concentrations of Zebularine was also tested.

FIG. 11A shows a RT-PCR analysis of p16 gene expression, as well as GAPDH, in T24 cells treated with either 50 µM or 100 µM of Zebularine for the indicated time points (Day 5, Day 7, Day 14, Day 21, Day 27, Day 33, and Day 40). For instance for Day 5 time point, this would indicate that the T24 cells were continuously treated with either 50 or 100 ρM of Zebularine for five days, and the mRNA levels of p16 and GAPDH (internal control) were assessed.

The methylation of both p16 promoter and p16 exon 2 in T24 cells treated with the 100 µM Zeb for those indicated times is quantified and summarized in FIG. 11B. The maximum demethylation of 100 µM Zeb occurs at Day 14, which dropped down from ~96% to ~47%. This drop of inhibition if similar to the effects observed with 5-Aza-CdR, the deoxy analog and the more potent version of the known inhibitor.

Example 4

Reactivation of Tumor Supressor Expression

This example provides evidence that treatment with Zebularine is effective to reactivate tumor suppressor expression in mammalian cell lines.

Methods and Materials

Quantitation of DNA Methylation by Ms-SNuPE

The average methylation at defined CpG sites was quantitated using a Ms-SNuPE assay, as described by Gonzalgo and Jones (*Nucleic Acids Res.* 25:2529-2531, 1997) and U.S. Pat. No. 6,251,594. Briefly, genomic DNA (~4 µg) was digested overnight with 4 units of EcoRI (Boehringer Mannheim) (p16 promoter/exon 1 and p16 exon 2; FIG. 9A) or with 4 units of RsaI (Boehringer Mannheim) (P3; FIG. 9B) to cut outside the region of interest.

After standard treatment with sodium bisulfite, a PCR product of the region was generated as template for top-strand methylation analysis. The sequences of the primers used for bisulfite-treated DNA amplification were as follows:

p16 Promoter/Exon 1:

```
                                         (SEQ ID NO: 5)
    sense,      5'-GTAGGTGGGGAGGAGTTTAGTT-3';
    and (SEQ ID NO: 6)
    antisense,  5'-TCTAATAACCAACCAACCCCTCCT-3'.
``` p16 Exon 2:

```
                                         (SEQ ID NO: 7)
    sense,      5'-TTGATTATTTTGTTTTTTTTGGTAGGTT-3';
    and (SEQ ID NO: 8)
    antisense,  5'-CAAATTCTCAAATCATCAATCCTCACCT-3'.
``` p3:

```
                                         (SEQ ID NO: 9)
    sense,      5'-GTTTATAGGTTTAGAGGTTTT-3';
    and (SEQ ID NO: 10)
    antisense,  5'-AACACATAAACCTATTTTAAACTTA-3'.
```

PCR Conditons:

p16 promoter/exon 1: 94° C. for 3 minutes, 94° C. for 45 seconds, 67° C. for 45 seconds, and 72° C. for 45 seconds for 40 cycles, with a final extension step at 72° C. for 10 minutes.

p16 exon 2: 94° C. for 3 minutes, 94° C. for 1 minute, 62° C. for 45 seconds, and 72° C. for 45 seconds for 40 cycles, with a final extension step at 72° C. for 10 minutes.

P3: 95° C. for 2 minutes, 95° C. for 1 minute, 50° C. for 50 seconds, and 72° C. for 1 minute for 40 cycles, with a final extension at 72° C. for 10 minutes.

The PCR product was electrophoresed and isolated from a 2% agarose gel, using Qiaquick Gel Extraction Kit (Qiagen), and the template eluted in a final volume of 30 μL double-distilled H₂0.

Duplicates of 4 μl of template were then added to 6 μl of mixture consisting of 1× PCR buffer, 1 μM final concentration primers, 1 μCi of [$^{32}$P]dCTP or dTTP, and 1 unit 1:1 Taq/TaqStart antibody (Clontech, Palo Alto, Calif.). Single nucleotide extension involved incubation at 95° C. for 1 minute, then 50° C. for 2 minutes, and finally 72° C. for 1 minute (p16 promoter/exon1 and P16 exon 2) and 95° C. for 1 minute, then 46° C. for 30 seconds, and finally 72° C. for 20 seconds (P3). The sequences for SNuPE primers were as follows:

p16 Promoter/Exon 1:

```
5'-TTTGAGGGATAGGGT-3';              (SEQ ID NO: 11)

5'-TTTTAGGGGTGTTATATT-3';           (SEQ ID NO: 12)
and

5'-TTTTTTTGTTTGGAAAGATAT-3'.        (SEQ ID NO: 13)
``` p16 Exon 2:

```
5'-GTTGGTGGTGTTGTAT-3';             (SEQ ID NO: 14)

5'-AGGTTATGATGGGTAG-3';             (SEQ ID NO: 15)
and

5'-TATTAGAGGTAGTAATTATGTT-3'.       (SEQ ID NO: 16)
``` p3:

```
5'-GGTATAGTTTGAGTAT-3';             (SEQ ID NO: 17)

5'-TTTTATTTATTGTTATTATGG-3';        (SEQ ID NO: 18)
and

5'-TATTTTTTAATAGTATTATTTTTTAT-3'.   (SEQ ID NO: 19)
```

After briefly spinning down the tubes, 4 μl of stop solution were added to the 10-μl reaction volume, and the samples were boiled for 5 minutes at 95° C. before loading 1.5 μl onto a 15% denaturing polyacrylamide gel (7 M urea). The gel was run at 90 W for 1.5 hours and then dried at 80° C. for 40 minutes. The gel was exposed to a phosphorimaging cassette for quantitation of the ratio of [$^{32}$P]dCTP versus [$^{32}$P]dTTP incorporation, and the quantitation of the percent methylation was averaged from three separate CpG sites. The gel was then exposed to BioMax MR film (Kodak) to record experimental results.

Determination of Cytotoxicity

10T1/2 (250/60-mm dish) and T24 cells (100/60-mm dish) were plated in triplicate sets for a colony-formation assay. 10T1/2 cells and T24 were treated with indicated concentrations of compounds. Once cell colonies were visible (after 12-14 days), cells were fixed in 100% methanol and stained with 10% Giemsa stain. The percentage cell survival was assessed by dividing the mean colony number on the treated plates divided by the mean colony number on the untreated plates ×100.

Results

Effects of Zebularine on DNA Methylation and Cytotoxicity in 10T1/2 Cell Line

Since 10T1/2 cells can be induced to differentiate into muscle by the demethylating action of either 5-Aza-CR or 5-Aza-CdR, the ability of Zeb to inhibit DNA methylation was examined and compared with these two drugs. The inhibition of DNA methylation by these three drugs, as assayed by Ms-SNuPE, is shown in Table 2. Treatment with 0.3 μM 5-Aza-CdR resulted in an effective methylation of 54% as compared to the control of 86%, while 3 μM 5-Aza-CR resulted in an effective methylation of 59% and 30 μM Zebularine resulted in an effective methylation of 58% (Table 2).

TABLE 2

Inhibition of DNA Methylation in 10T 1/2 Cells

| Treatment | Conc. (μM) | Muscle Formation | % Methylation | Ave. Plating Efficiency (%) |
| --- | --- | --- | --- | --- |
| Control | 0 | 0 | 86 +/− 1 | 22 |
| 5-Aza-CdR | 0.3 | +++ | 54 +/− 5 | 5 |
| 5-Aza-CR | 1 | ++ | 65 +/− 2 | 21 |
|  | 3 | +++ | 59 +/− 6 | 16 |
| Zebularine | 10 | + | 75 +/− 2 | 20 |
|  | 30 | ++ | 58 +/− 1 | 18 |

10T1/2 cells were treated with the indicated cytidine analogs for 24 hours and scored for muscle cells 9-10 days later as + to +++ (with + representing minimal muscle formation and +++ representing maximal muscle formation). To determine the inhibition of DNA methylation, the p3 locus was assayed for percentages of methylation using Ms-SNuPE analysis. Cell killing was determined by the lowering of plating efficiency in similarly treated cultures containing 250 cells and stained with Giemsa stain after 14-16 days. Results are the mean values obtained for triplicate dishes in two separate experiments.

Table 2 also shows the cytotoxicity, as measured by decrease in plating efficiency, of all three drugs on cultured 10T1/2 cells. A dose of 0.3 μM 5-Aza-CdR is considerably more cytotoxic than either 3 μM 5-Aza-CR or 30 μl Zebularine (74% vs. 24% vs. 17% decrease in plating deficiency, respectively, Table 2). However, it was observed that both 0.3 μM 5-Aza-CdR and 3 μM 5-Aza-CR caused appreciable cell death while 30 μM Zebularine caused only very little cell death.

Effects of Zebularine on DNA Methylation in Human Tumor Cells

Both p16 promoter and exon 2 loci are frequently methylated in bladder cancer cell lines and tumors, and demethylation of p16 promoter has been noted previously to correspond directly with p16 expression (Gonzalez-Zulueta et al., *Cancer Res.* 55:4531-4537, 1995; Bender et al., *Cancer Res.* 58:95-101, 1998). Given that p16 gene expression can be induced by all three drugs tested (FIG. 8), the effectiveness of these drugs in demethylating both p16 promoter and p16 exon 2 was further investigated by Ms-SNuPE analysis.

From FIG. 10, it can be seen that treatment with 3 μM 5-Aza-CdR resulted in a decrease in the methylation of p16 promoter from 96% to 52% (Table 3). Increasing concentrations of 5-Aza-CR showed decreasing levels of methylation, starting from methylation level of 91% with the 3 μM dose down to 68% with the 100 μM dose in the p16 promoter (Table 3).

Treatment with 300 μM, 500 μM, and 1 mM Zebularine for 24 hours resulted in a decrease in the methylation levels of p16 promoter to 91%, 85%, and 72%, respectively (Table 3). Prolonging the treatment with 300 μM, 500 μM, and 1 mM Zebularine for 48 hours showed a more pronounced inhibition of methylation, with methylation levels of p16 promoter decreased to 80%, 77%, and 68%, respectively (Table 3). This demethylating pattern correlated well, but not linearly. with the p16 expression analysis shown in FIG. 8. These results suggested that the reactivation of p16 expression by Zebularine and 5-Aza-CR correlated with the inhibition of methylation in both p16 promotor and exon 2 regions.

Table 3 also shows the cytotoxicity, as measured by decrease in plating efficiency, of all three drugs on cultured T24 cells. A dose of 3 µM 5-Aza-CdR is extremely cytotoxic (75% decrease in plating efficiency). 5-Aza-CR showed dose-dependent cytotoxicity, with extremely minimal cytotoxic effects observed with the 3 µM dose to considerable cytotoxic effects observed with the 100 µl dose (54% decrease in plating efficiency). In contrast, Zebularine showed dose-dependent cytotoxicity with insignificant time-dependent cytotoxicity. In other words, the increase in the time of treatmaent did not signifcantly increase the cytotoxicity for any of the Zebularine doses. The highest cytotoxicity is observed in T24 cells treated with 1 mM Zebularine for 48 hrs (23% decrease in plating efficiency), which is considerably lower than that of either 5-Aza-CR or 5-Aza-CdR. These results demonstrate that Zebularine was much less cytotoxic that either 5-Aza-CR or 5-Aza-CdR in T24 cells, even at very high concentrations.

toxicity for any of the Zebularine doses. The highest cytotoxicity is observed in T24 cells treated with 1 mM Zebularine for 48 hrs (23% decrease in plating efficiency), which is significantly lower toxicity than either 5-Aza-CR or 5-Aza-CdR.

Example 5

Quantification of Uridine-Cytidine Kinase in Human Lung Tumors

This example provides a representative method for testing tissues for uridine-cytidine kinase activity. Since uridine-cytidine kinase is thought to be the first enzyme involved in activating Zebularine, its elevation in tumor tissue provides a mechanism for preferential activity of the drug in those tissues most in need of reduction of (or reversal of) DNA methylation.

Uridine Kinase Assay

Clinical biopsy tissue samples from human lung tumors, and parallel normal tissue samples, were suspended in a buffer containing 50 mM Tris HCl, pH 7.5, 5 mM benzamidine, 20% glycerol, and 5% $H_2O$. The buffer was taken to 2 mM DTT and 0.5 mM PMSF just before extraction. The tissue sample was homogenized in this mixture, then soni-

TABLE 3

Inhibition of DNA Methylation in T24 Cells

| Treatment | Concentration (µM) | Duration of Treatment (hrs) | p16 Promoter Methylation (%) | p16 Exon 2 Methylation (%) | Relative p16 Exon 2 De-methylation (%) | Toxicity (%) |
|---|---|---|---|---|---|---|
| Control | 0 | 24 | 96 +/− 1 | 96 +/− 1 | 0 | 0 |
| 5-Aza-CdR | 3 | 24 | 52 +/− 5 | 51 +/− 1 | 47 +/− 1 | 75 |
| 5-Aza-CR | 3 | 24 | 91 +/− 1 | 88 +/− 2 | 8 +/− 2 | 2 |
|  | 10 | 24 | 83 +/− 2 | 82 +/− 1 | 15 +/− 1 | 12 |
|  | 30 | 24 | 73 +/− 2 | 72 +/− 2 | 25 | 30 |
|  | 100 | 24 | 68 +/− 2 | 68 +/− 3 | 29 | 54 |
| Zebularine | 300 | 24 | 91 +/− 1 | 89 +/− 1 | 7 +/− 1 | 1 |
|  |  | 48 | 80 +/− 1 | 81 +/− 2 | 16 +/− 2 | 2 |
|  | 500 | 24 | 85 +/− 1 | 87 +/− 1 | 9 +/− 1 | 7 |
|  |  | 48 | 77 +/− 2 | 79 +/− 2 | 18 +/− 2 | 8 |
|  | 1000 | 24 | 72 +/− 2 | 77 +/− 2 | 20 +/− 2 | 18 |
|  |  | 48 | 68 +/− 2 | 73 +/− 1 | 24 +/− 1 | 23 |

Reduction of DNA Methytransferases in Zebularine-Treated Cells

Treatment of T24 cells with Zebularine caused a significant reduction in the levels of DNMT1 and DNMT3b3. The mRNA for DNMT3b3 is the only 3b transcript expressed in T24 cells, and DNMT3a levels could not be assessed because no suitable antibodies against DNMT3a are available. Thus, with reference to FIG. 12, protein extracts were isolated from both treated and untreated T24 (population 3 million cells, treated with 500 µM Zebularine for 48 h), and ot analysis with specific antibodies for DNMT1 and DNMT3b3 as shown in FIG. 12. β-actin was included as a loading control, and the molecular weights of each protein are indicated.

Cytotoxicity in Human Tumor Cells

FIG. 10B shows the cytotoxicity, as measured by decrease in plating efficiency, of all three drugs on cultured T24 cells. A dose of 3 µM 5-Aza-CdR is extremely cytotoxic (75% decrease in plating efficiency). 5-Aza-CR showed dose-dependent cytotoxicity, with the highest level in the 100 µM dose (54% decrease in plating efficiency). On the other hand, Zebularine showed dose-dependent cytotoxicity with slight time-dependent cytotoxicity. In other words, the increase in the time of treatment did not significantly increase the cytocated for 3 five-second pulses to disrupt the cells. The cell extract was centrifuged at 14,000 g at 4° C. for 10 minutes, and the supernatant removed.

Protein extraction was determined by the Bradford method using bovine serum albumin as the standard.

The kinase assay reaction mixture contained 50 mM $MgCl_2$, 5 mM ATP, and 85% $H_2O$. 2 mM DTT is added just before use. The reaction was initiated by adding 5 µl of 200 mM CP and CPK (1 unit/µl) to 150 µl of the reaction mix and incubating for 2 minutes at 37° C. Then, 500 µM of $^3$H labeled uridine was added and the sample incubated for 1 minute at 37° C. before the enzyme extract was added and incubated for a period of time ranging from 0-15 minutes. Reactions were terminated by heating in a boiling $H_2O$ bath for 2 minutes.

The amount of nucleotide formed was determined by spotting 20 µl aliquots of the reaction mixture onto DE-81 2.2 cm Whatman filter discs. After air drying, the nucleoside substrate was removed by washing the discs twice for 10 minutes in 1 mM ammonium formate and twice for 5 minutes in deionized water, with gentle stirring. It is useful to have a control sample, lacking enzyme that is assayed concurrently with each determination. The washed paper discs were heat dried and then placed into individual scintillation vials, and eluted for 30 minutes in 0.1M HCl-0.1 MKCl and then rocked for 10 minutes in scintillation mixture; activity was determined by scintillation counting. Enzyme activity is expressed in pmoles/minute/mg protein.

Data from these analyses are reported in Table 4. As illustrated in Table 4, 30% of the lung tumors had substantially higher levels of uridine/cytidine kinase (UKICK) than associated normal tissue.

TABLE 4

Uridine-Cytidine Kinase Activity in Human Tumors

Human Lung Tumors

| Patient | U/CK[1] T/N | Standard Deviation | T/N[2] |
|---|---|---|---|
| 1 | 3.86 / .863 | 2.1 / .29 | 4.5 |
| 2 | <2.36 / <1.52 | 1.7 / .68 | <1.6 |
| 3 | 2.98 / 5.8 | 6.1 / 2.8 | .51 |
| 4 | 27.6 / 14.8 | 5.6 / 9.8 | 1.9 |
| 5 | 18.6 / 5 | 3.9 / 1.6 | 3.7 |
| 6 | 29.3 / 5.34 | 7.1 / .98 | 5.5 |
| 7 | 25.9 / 6.42 | 3.8 / .09 | 4.0 |
| 8 | 8.59 / 11.9 | .58 / .07 | .72 |
| 9 | 46.9 / 54.1 | .99 / 15 | .87 |
| 10 | 32.8 / 57.8 | 1.7 / 1.2 | .57 |
| 11 | 194 / 34.4 | 15 / 6.4 | 5.6 |
| 12 | 18 / 13.4 | 4.8 / 6.3 | 1.3 |
| 13 | 48 / 34.9 | 14 / 3.6 | 1.4 |
| 14 | 21.4 / <2.07 | 1.8 / .90 | 10 |

| Patient | U/CK T/N | Standard Deviation | T/N |
|---|---|---|---|
| 15 | 67.2 / 72.2 | .22 / 5.0 | .93 |
| 16 | 31.2 / 100 | 12.9 / 4.2 | .31 |
| 17 | <2.48 / 96.4 | .35 / 14 | <0.03 |
| 18 | 52.5 / 53.7 | 2.7 / 11 | .98 |
| 19 | 31.6 / 112 | .35 / 14 | .28 |
| 20 | 46.2 / 46.4 | 1.3 / 8.4 | 1.0 |
| 21 | 19.7 / 128 | 16 / 100 | .15 |
| 22 | .540 / .322 | .41 / .04 | 1.7 |
| 23 | 84.1 / 22.8 | 15 / .64 | 3.7 |
| 24 | 66.3 / 20.1 | 19 / 1.8 | 3.3 |
| 25 | 61.4 / 46.1 | 16 / 8.4 | 1.3 |
| 26 | 55.6 / 37.8 | 20 / 3.2 | 1.4 |
| 27 | 52.9 / 64.7 | 9.6 / 7.2 | .82 |

8/27 30% T/N > 2

| Patient | U/CK T/N | Standard Deviation | T/N |
|---|---|---|---|
| Human Breast Tumors | | | |
| 1 | 1.48 / 42.0 | .92 / 1.2 | 0.4 |
| 2 | 210 / 459 | 11 / 1.4 | .46 |
| 3 | 100 / 33.6 | .92 / 2.9 | 3.0 |
| Human Rectal Tumors | | | |
| 1 | 20.3 / 24.9 | 3.9 / 7.3 | .82 |
| 2 | 109 / 19.9 | 28 / 2.7 | 5.5 |
| 3 | .895 / 43.4 | .18 / 26 | .02 |

[1]U/CK: uridine/cytidine Kinase pmoles/min/mg protein; values for tumor appear over values for normal tissue
[2]Ratio of activity in tumor/activity in adjacent paired normal tissue Example 6

In vivo Effects of Zebularine

This example describes in vivo effects of Zebularine on EJ6 tumors in BALB/c nu/nu mice. Furthermore, Example 6 demonstrates the efficacy of Zebularine against human tumor cells.

Materials and Methods

EJ6 cells ($5 \times 10^5$/injection) were inoculated subcutaneously into the right and left flanks of male BALB/c nu/nu mice at 4-6 weeks of age (available from Harlan, San Diego, Calif.). Zebularine treatments were initiated after macroscopic (50-200 mm 3) tumor formation (4-6 weeks later). Zebularine (500 mg/kg or 1000 mg/kg) was administered daily via intraperitoneal injection or oral gauage feeding over a period of 18 days. Control mice received 0.45% saline administered via intraperitoneal injection or oral gavage feeding over a period of 18 days. Mice (n=30) were divided into five groups (control group, 500 mg/kg intraperitoneal injection, 500 mg/kg oral, 1000 mg/kg intraperitoneal injection, and 1000 mg/kg oral). Each treatment group consisted of a minimum of five animals (at least 6 tumors per group).

Tumor volumes (TV) were measured with calipers and calculated using the following formula: tumor volume=$LD^2/2$ (where L is the longest diameter and D is the shortest diameter). The relative tumor volume (RTV) was calculated as: RTV=$TV_n/TV_o$, where $TV_n$ is the calculated volume at day n. Animals were sacrificed 24 hours after the last treatment. Tumors were removed, immediately fixed with neutral buffered formalin and then embedded in OCT compound for frozen sections. The frozen sections were processed and stained with hematoxylin and eosin (H&E). All histological examinations were carried out by light microscopy using a Leica DM LB microscope (Leica Microsystems, Germany).

Total RNA was isolated from the tumors to analyze gene expression using conventional methods. DNA also was isolated, to measure the methylation status of p16 promoter by Ms-SnuPE as described below.

Results

Tumor sections from control and treated mice groups were cut and analyzed by H&E staining. Representative images of the whole field of tumor sections taken from each group were compared. A lower ratio of tumor cells to stroma in treated versus untreated tumor sections was observed by inspection of the stained sections.

Tumor volume was measured for all mice groups at the time points indicated in FIG. 13. Similarly, each group of mice (n=5 or 6) was weighed at the indicated time points, and average body weight was plotted against days after initial treatment in FIG. 14. In summary, as shown in FIG. 13, tumor growth appeared suppressed in all treated groups as compared to the control group, and tumor regression was observed with the groups that were treated with 1000 mg/kg orally or intra-peritoneally. As shown in FIG. 14, weight loss was minimal in all treated groups, with the greatest weight loss (~7%) observed in the group treated with 1000 mgtkg. Furthermore, reactivation of p16 was demonstrated as described below.

Zebularine Reactivates p16 Gene Expression in Vivo

Reactivation of p16 gene expression after treatment with Zebularine was detected via RT-PCR with primers specific for human p16 cDNA in EJ6 tumor cells growing in BALB/c nu/nu mice. GAPDH mRNA levels were measured to control for the quantity and integrity of the input RNA. The control group represents tumors obtained from mice mock-treated either with 0.45% NaCl via intraperitoneal injection or oral gavage feeding. Results from one of six similar independent tumors are shown for each group in FIG. 15.

The methylation status of p16 promoter of the DNA isolated from EJ6 tumor cells from the representative groups was quantitated using Ms-SnuPE analysis. The results, FIG. 16, were an average of three CpG sites from 4 independent tumors in each group performed in duplicate.

Example 7

Metabolism of Zebularine

Zebularine metabolites were identified after incubation of human bladder cancer cells (T24) in DMEM+10% FCS medium with antibiotics. Zebularine (10 μM, 1 μCi), specific activity 200 DPM/pmole was used in these experiments. At the end of the incubation, cells were extracted with 60% methanol and aliquots were analyzed by SAX-10 HPLC using a methanolwater gradient as follows: 1-5 min 1% MeOH, 5-25 min gradient to 25% MeOH, 25-35 min isocratic with 25% MeOH and back to 1% MeOH after 10 min. The phosphorylated metabolites were identified by comparison with authentic synthetic standards. Using this methodology formation of metabolites as a function of concentration after a 6 hr incubation period was investigated (FIG. 17). The major metabolite formed was the 5'-triphosphate. On the other hand, a single dose of Zebularine (10 μM, 1 μCi), after a 24 hr incubation period revealed the formation of an unknown metabolite (?2, FIG. 18) that could be important in mediating the action of the drug.

Following a similar incubation protocol in T24 cells (Zebularine (10 μM, 1 μCi) for 24 hr, cellular DNA and RNA were isolated by the tri-reagent method according to the manufacture's instructions. Levels of Zebularine and 2'-Deoxyzebularine were determined by measuring total radioactivity in purified RNA and DNA, respectively. The identity of Zebularine and 2'-Deoxyzebularine was accomplished by a reverse phase HPLC analysis of digested RNA and DNA and comparison against authentic standards. In FIG. 19 a bar graph depicts the relative incorporation of Zebularine into DNA and RNA in T24 cells, showing that approximately 7 times the amount of Zebularine is incorporated into RNA as DNA.

This disclosure provides embodiments for using Zebularine, and derivatives thereof, to inhibit DNA methylation. The method further provides means of treating or ameliorating hypermethylation-related diseases, such as hypermethylation-related cancers, by administering Zebularine (or a derivative thereof) to the subject. It will be apparent that the precise details of the disclosure may be varied or modified without departing from the spirit of the described invention. We claim all such modifications and variations that fall within the scope and spirit of the claims below.

---

We claim:

1. A method of reducing, inhibiting or reversing nucleic acid methylation in vivo, comprising:
    comparing the uridine-cytidine kinase level and the methylation state of a mammalian tumor tissue sample to the uridine-cytidine kinase level and the methylation state of a mammalian non-tumor tissue sample to determine whether the mammalian tumor tissue sample has an elevated uridine-cytidine kinase level and an elevated methylation state compared to the mammalian non-tumor tissue sample, wherein the mammalian tumor tissue sample and the mammalian non-tumor tissue sample are from the same tissue type;
    based on the comparative determination, selecting a mammalian tumor having an elevated uridine-cytidine kinase level and having a hypermethylated DNA sequence that comprises a regulatory region of a tumor suppressor gene; and
    reducing, inhibiting or reversing DNA methylation in the mammalian tumor in vivo, wherein the reducing, inhibiting or reversing DNA methylation in the mammalian tumor in vivo consists of administering a hypomethylating effective amount of Zebularine, or Zebularine in combination with tetrahydrouridine, to the mammalian tumor having the elevated level of uridine-cytidine kinase and the hypermethylated DNA sequence.

2. The method of claim 1, wherein the Zebularine inhibits a DNA methyltransferase.

3. The method of claim 1, wherein the hypermethylated DNA sequence comprises a CpG dinucleotide.

4. The method of claim 1, wherein reducing, inhibiting or reversing DNA methylation ameliorates a tumorigenic state of the mammalian tumor having a level of uridine-cytidine kinase elevated above normal levels.

5. The method of claim 1, wherein the mammalian tumor is selected from the groups consisting of breast, prostate, lung, renal, bladder, squamous cell, ovarian, rectal and metastatic tumors.

6. The method of claim 1, wherein the tumor suppressor gene is selected from the group consisting of cadherin, estrogen receptor, VHL, H19, 14-3-3 σ, Apaf-1, p53, p16, glutathione-S-transferase, methyl guanine methyltransferase and tissue inhibitor of metalloproteinase-3.

* * * * *